(12) United States Patent
Franklin-Lees et al.

(10) Patent No.: US 6,593,528 B2
(45) Date of Patent: Jul. 15, 2003

(54) MEDICAL DEVICE INTERFACE SYSTEM

(75) Inventors: David Franklin-Lees, Bucks (GB); James E. Gharib, San Diego, CA (US)

(73) Assignee: Alaris Medical Systems, Inc., San Diego, CA (US)

( * ) Notice: Subject to any disclaimer, the term of this patent is extended or adjusted under 35 U.S.C. 154(b) by 0 days.

(21) Appl. No.: 10/143,125

(22) Filed: May 10, 2002

(65) Prior Publication Data

US 2002/0134570 A1 Sep. 26, 2002

Related U.S. Application Data

(62) Division of application No. 09/444,328, filed on Nov. 19, 1999, now Pat. No. 6,407,335.

(51) Int. Cl.$^7$ ................................................ H01H 9/02
(52) U.S. Cl. ........................... 174/58; 174/50; 174/59; 361/686
(58) Field of Search ........................... 174/50, 58, 52.1, 174/52.4, 17 R, 135, 59; 361/683, 684, 685, 686; 248/56, 229.25, 227.4, 230.6; 600/301, 300; 220/241, 3.8

(56) References Cited

U.S. PATENT DOCUMENTS

| | | | |
|---|---|---|---|
| 3,888,446 A | 6/1975 | O'Brien et al. | ............. 248/231 |
| 4,674,722 A | 6/1987 | Danby et al. | ............. 248/231.3 |
| 4,700,922 A | 10/1987 | Gross | ........................ 248/558 |
| 4,895,161 A * | 1/1990 | Cudahy et al. | ............. 600/301 |
| 4,970,900 A * | 11/1990 | Shepherd et al. | ............ 600/488 |
| 5,024,225 A * | 6/1991 | Fang | ............................ 174/50 |
| 5,431,509 A * | 7/1995 | Anderson et al. | ...... 248/225.11 |
| 5,566,676 A * | 10/1996 | Rosenfeldt et al. | .......... 600/481 |
| 5,575,807 A * | 11/1996 | Faller | ............................ 607/5 |
| 5,685,314 A | 11/1997 | Geheb et al. | ................ 128/700 |
| 5,829,723 A * | 11/1998 | Brunner et al. | ......... 248/222.13 |
| 6,115,242 A * | 9/2000 | Lambrecht | .................. 257/686 |
| 6,115,250 A * | 9/2000 | Schmitt | .................. 165/104.34 |
| 6,183,417 B1 * | 2/2001 | Geheb et al. | ................ 600/301 |
| 6,191,943 B1 * | 2/2001 | Tracy | .......................... 361/679 |
| 6,407,335 B1 * | 6/2002 | Franklin-Lees et al. | ....... 174/50 |
| 6,434,001 B1 * | 8/2002 | Bhatia | ......................... 361/687 |

FOREIGN PATENT DOCUMENTS

| | | | |
|---|---|---|---|
| DE | 196 21 029 C1 | 2/1997 | .......... A61G/13/10 |
| EP | 0 780 134 A1 | 6/1997 | |

* cited by examiner

*Primary Examiner*—Dean A. Reichard
*Assistant Examiner*—Angel R. Estrada
(74) *Attorney, Agent, or Firm*—Fulwider Patton Lee & Utecht, LLP

(57) ABSTRACT

An interface device secures an instrument to a docking station having a casing having at least one signal port and a mounting rail mounted within a recessed portion of the casing. The signal ports may be power or data communications ports. A back panel forms part of an instrument housing for housing the instrument, a first portion protrudes rearward from the back panel and a first recess is carried by the protruding portion. The first recess is dimensioned to receive the mounting rail. A rail cam is rotatably mounted within the protruding portion and is aligned with the first recess to receive and retain the mounting rail and at least one first-portion signal port carried by the first portion. The first portion is dimensioned to fit within the recessed portion of the casing such that the rail cam is positioned to receive the mounting rail and the at least one first-portion signal port is aligned, in a complementary fashion, with the at least one casing signal port. A pole clamp assembly may be positioned near the first and second portions. A pivot member is moveable between a retracted position and an extended position and a post having an axis. The post is mounted to the pivot member for axial movement and mounted thereto such that when the pivot member is retracted the axis of the post is substantially parallel with the back panel and when the pivot member is extended the axis of the post is substantially perpendicular to the back panel.

22 Claims, 17 Drawing Sheets

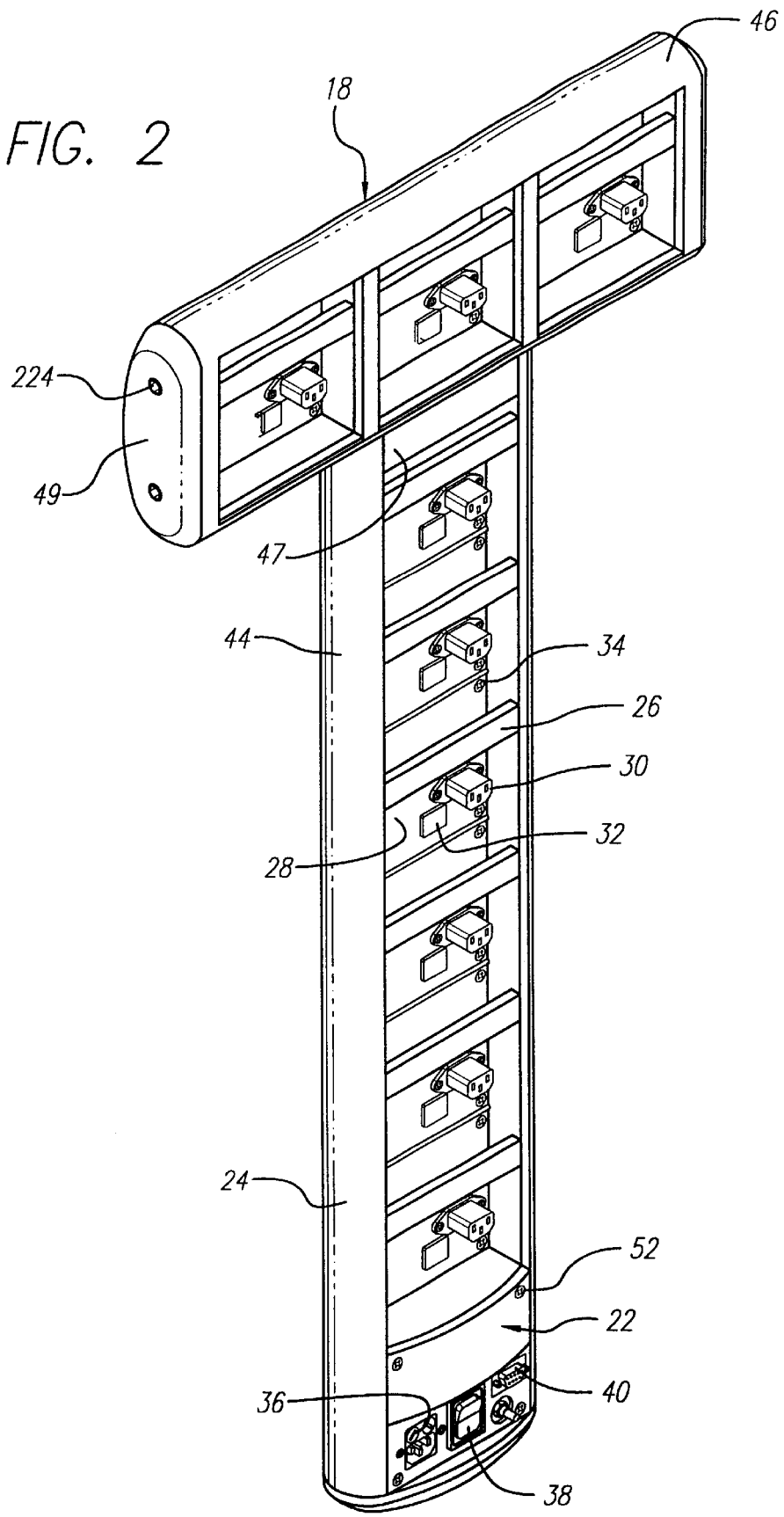

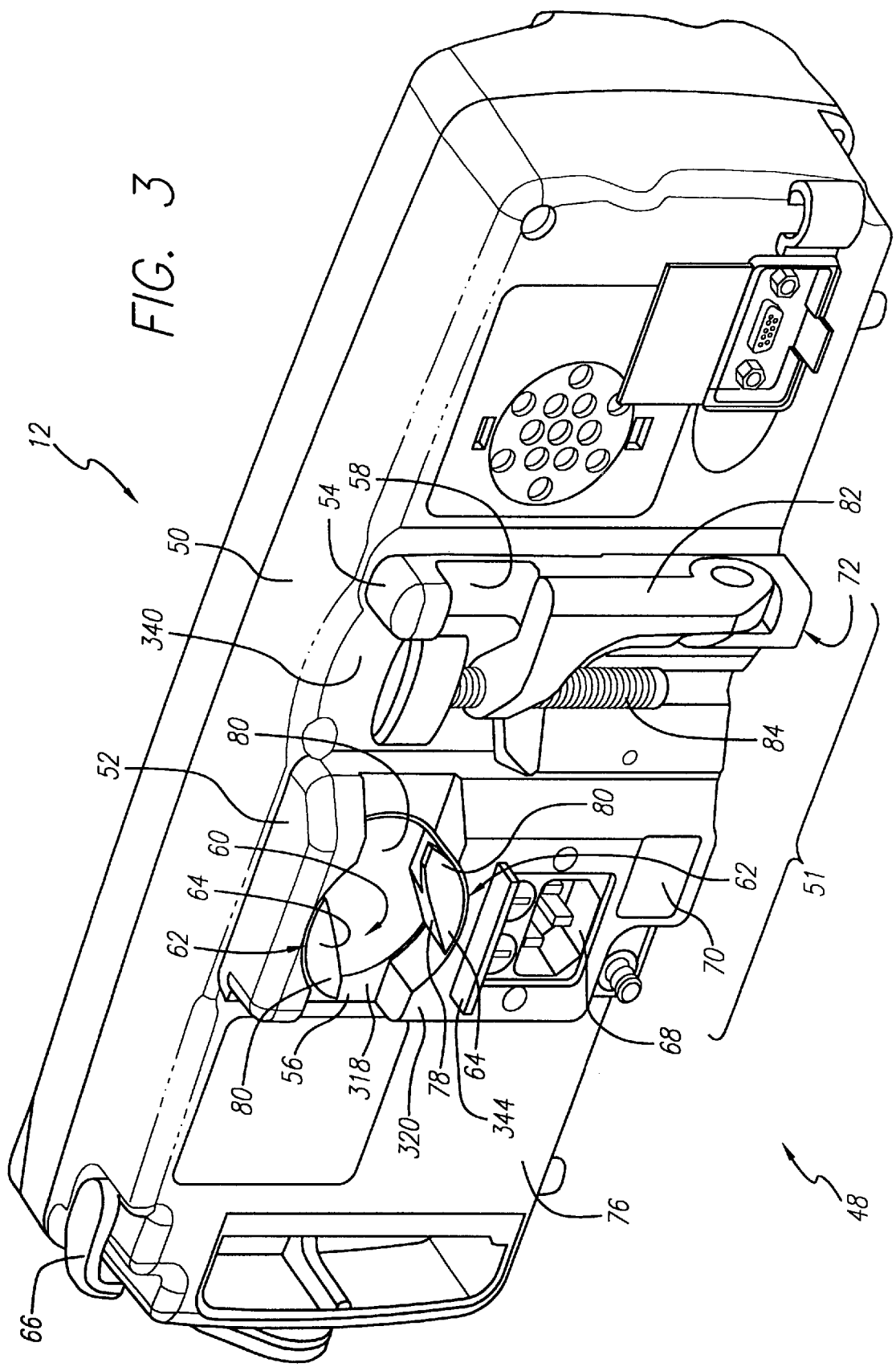

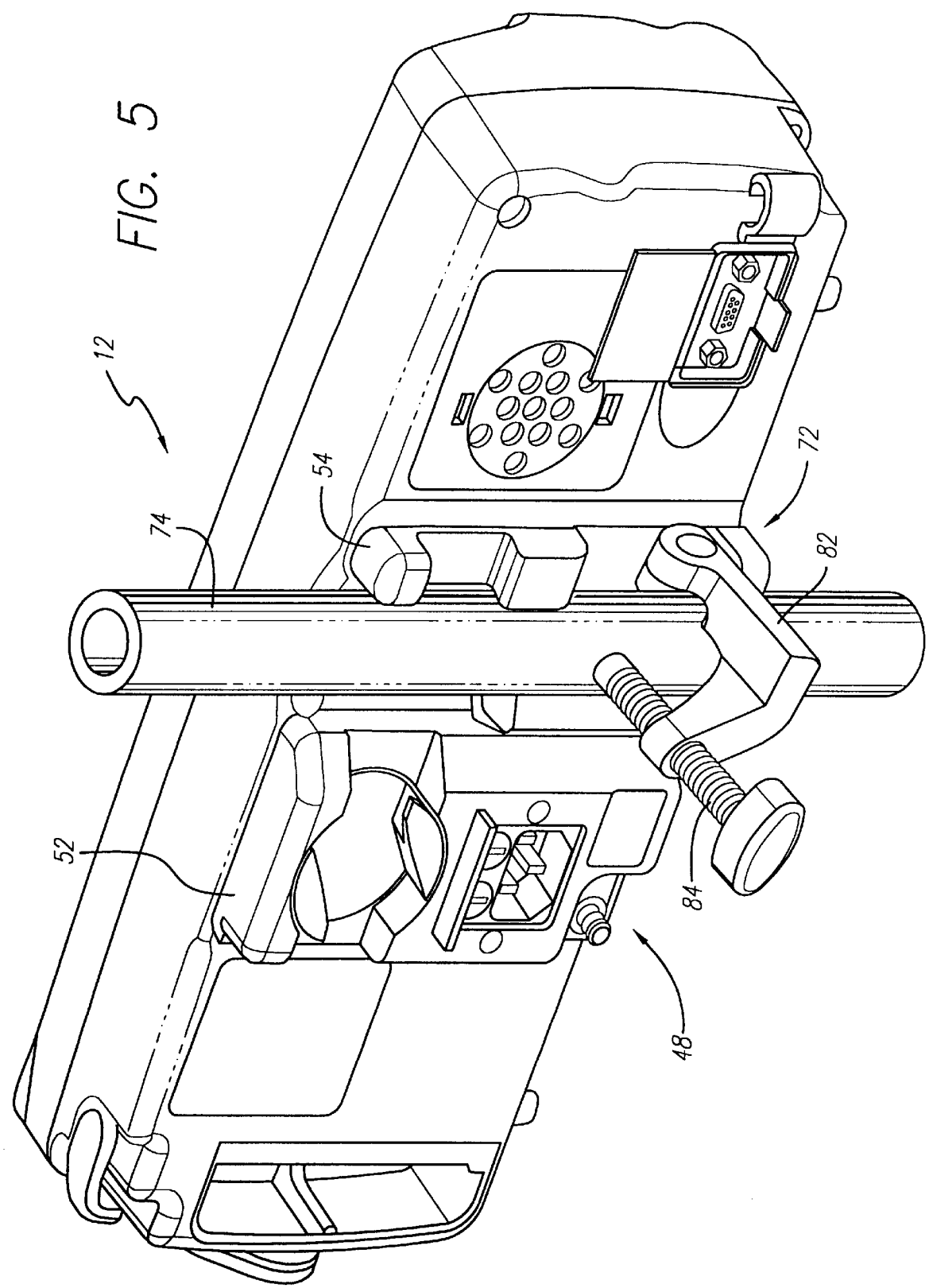

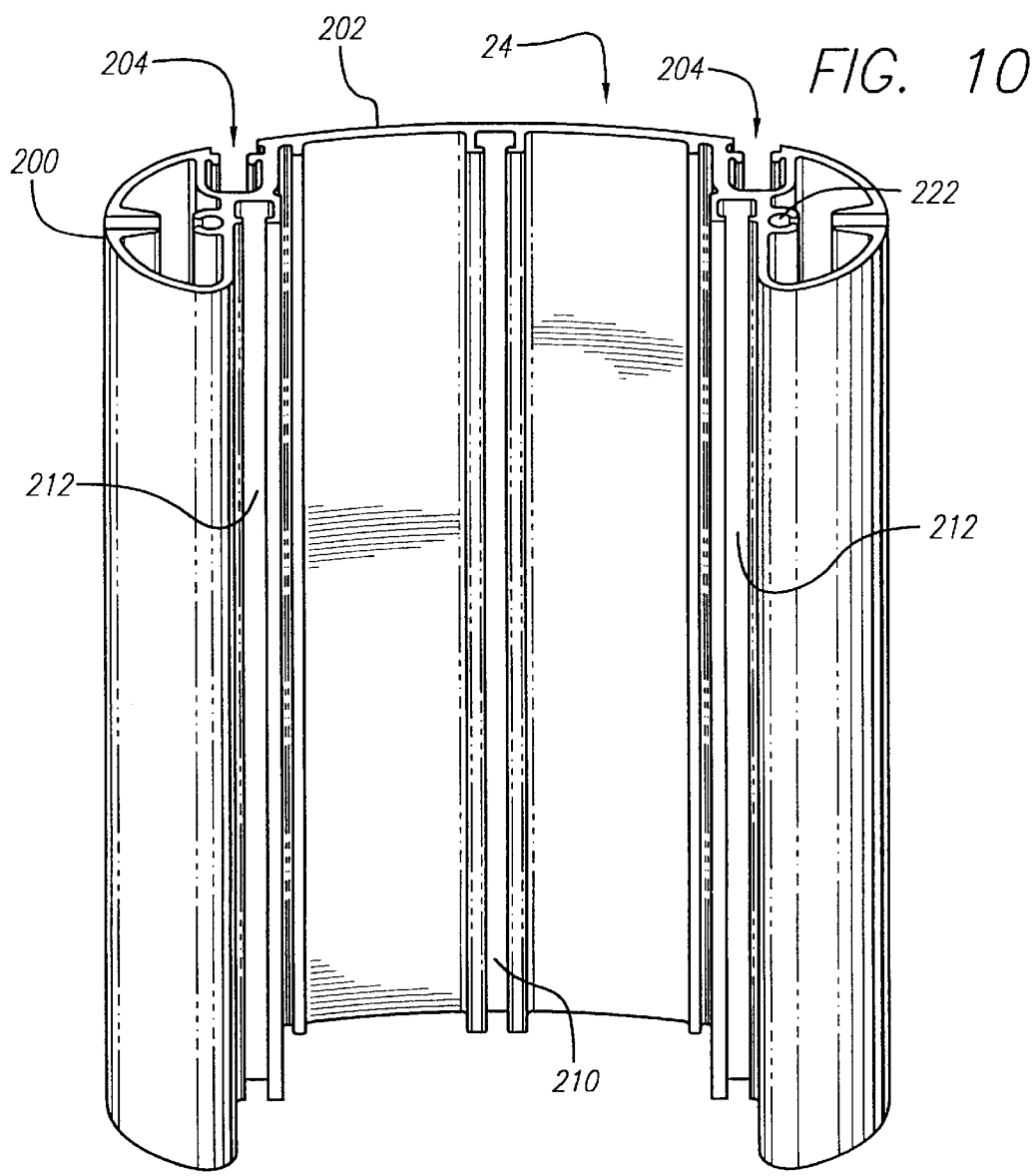
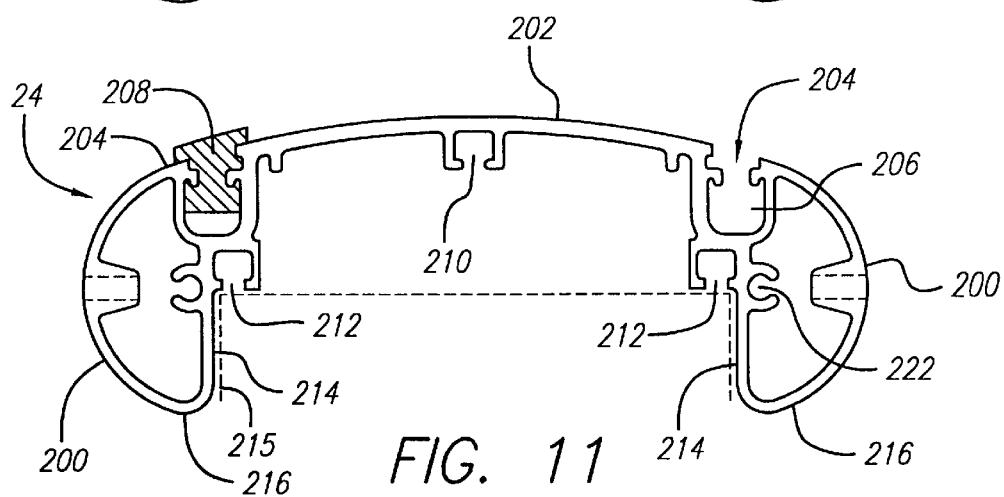
FIG. 10
FIG. 11

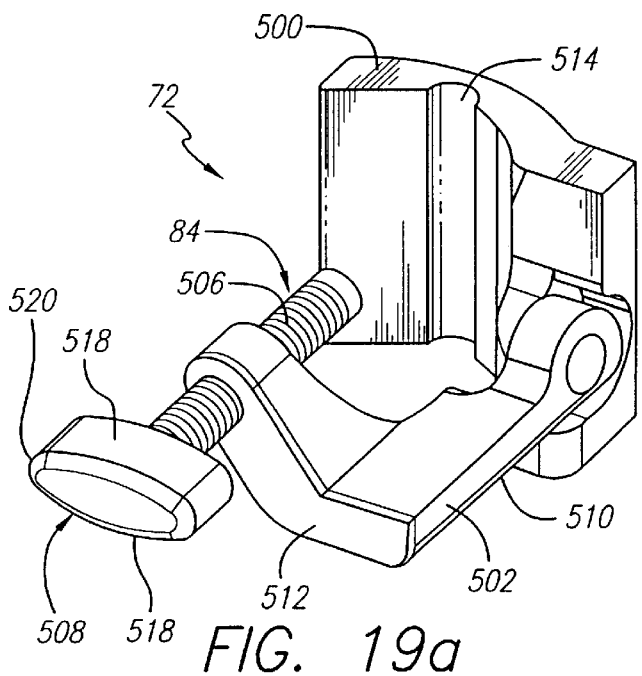
FIG. 19a
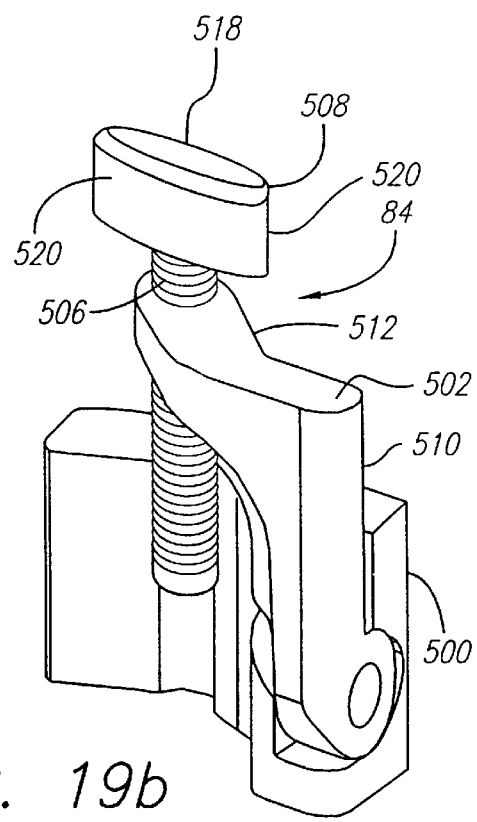
FIG. 19b
FIG. 19c
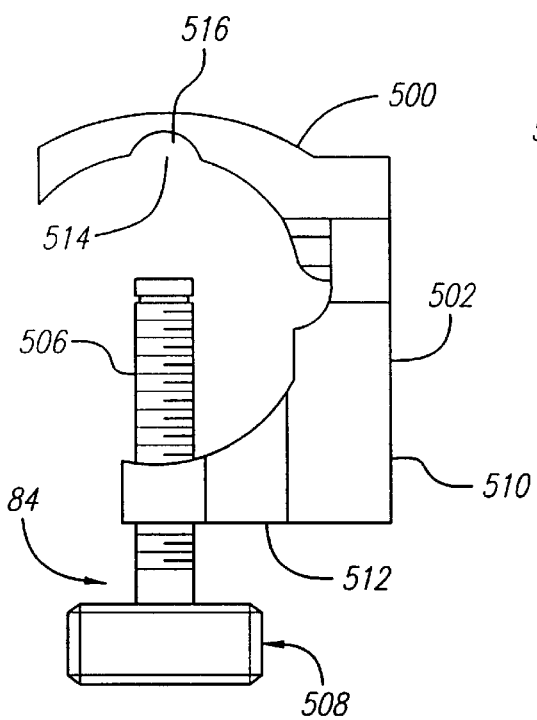
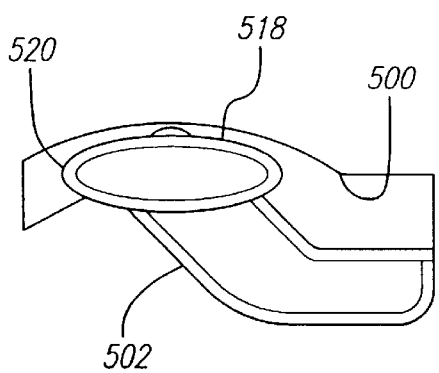
FIG. 19d

MEDICAL DEVICE INTERFACE SYSTEM

This is a division of application Ser. No. 09/444,328 filed Nov. 19, 1999 now U.S. Pat. No. 6,407,335.

BACKGROUND OF THE INVENTION

The invention relates generally to a medical device interface system, and more particularly, to an interface for securing a medical device to a mounting device such as a rail or a pole. The invention further relates to instrument docking devices providing power and electrical communications between an instrument, associated with the interface, and an external device.

In today's hospital environment, it is common for multiple medical devices, e.g., syringe pumps, infusion pumps, vital signs monitoring devices, to be simultaneously used to treat and monitor an individual patient. In such situations the instruments are typically secured to a mounting device positioned near the patient. A commonly used mounting device is a mounting rail or bar having standard height and depth dimensions. Typically, such rails are mounted to the walls of a hospital room at various heights and run the entire length of the room. The rails are spaced outward from the wall on spacers to allow for the placement of a fastening device between the wall and the back of the rail. A typical device for securing a medical device to a mounting rail is an L-bracket and a screw clamp. The L-bracket is mounted to the back of an instrument near the top and positioned such that when the instrument is mounted to the rail the bracket rests on the top and extends downward behind the back of the rail. The screw clamp is located on the rear of the instrument and is positioned such that when tightened the screw clamps against the back of the rail. This mounting device is somewhat inconvenient in that it requires the turning of a clamp screw in space that is typically too small to comfortably accommodate hand movement.

Another common mounting device is a pole, such a free-standing pole or one associated with the patient's bed. Pole clamps have commonly been used and have been rigidly mounted to the backs of medical devices. However, unless they are configured to be movable out of the way, they can interfere with other mounting arrangements of the instrument. Such stationary clamps can also cause inconvenience in handling and storage of the instrument due to the protrusion of the clamp. Hence those skilled in the art have recognized a need for a more versatile pole clamp.

Once the medical devices are properly secured to a mounting device the instruments must be connected to a power outlet. To this end, each individual power cord of each individual instrument is plugged into a power outlet located in the wall or in a power strip extension cord having multiple power outlets. Providing power connections in this manner may be problematic in that cables may become tangled thus rendering the tracing of an individual cable to its associated outlet and the subsequent movement of an individual instrument difficult. Safety issues also arise in that the use of a power strip extension cord to accommodate multiple instruments may cause a power outlet to be overloaded. Furthermore, the more cables that are laying on a hospital floor, the higher the risk of entanglement with a patient or care provider. In addition to the power cords, most medical devices also require or can accommodate a data communications connection to an external device 'such as a computer. The connection of individual data communications cables to each device further increases the forgoing problems and difficulties.

Hence, those skilled in the art have recognized a need for an interface capable of mounting an instrument to either a mounting rail or a pole. The need has also been recognized for a docking station capable of accepting a plurality of instruments and providing power and communications signals to the instruments through the docking station instead of through individual cables. The present invention fulfills these needs and others.

SUMMARY OF THE INVENTION

Briefly and in general terms, the invention is directed to a device interface system for securing a medical device to a mounting device such as a rail or a pole. The invention is further directed to an instrument docking device for providing power and electrical communications between an instrument, associated with the interface, and an external device.

In a first aspect, the invention relates to an interface forming part of an instrument housing for securing the instrument housing to a mounting rail mounted to a surface. The interface includes a back panel, a first portion protruding rearward from the back panel and a first recess carried by the protruding portion. The first recess is dimensioned to receive the mounting rail. The interface further includes a rail cam rotatably mounted within the protruding portion. The rail cam is aligned with the first recess to receive and retain the mounting rail.

In a detailed aspect of the interface, the protruding portion further carries a circular cutout partially within the first recess, and the rail cam includes a circular cam base having a surface substantially subflush with the first recess. The base is mounted for pivotal movement within the circular cutout. The rail cam further includes two opposing arms near the periphery of the cam base. The arms extend substantially perpendicular relative the surface of the cam base and each arm has an arm base defining a lock surface. The arms are positioned on the cam base such that the distance between the two lock surfaces is large enough to receive the mounting rail. In a further detailed facet of the interface, each arm further includes a guiding portion at the top of the arm base for contacting the mounting rail during insertion of the rail cam onto the mounting rail and transferring the force of contact with the mounting rail to the cam base to therein induce rotation of the rail cam.

In another detailed facet, the mounting rail has a height and depth and the guiding portion of each rail-cam arm includes a first portion sloping downward from a first height near the outer periphery of the arm base to a second height inward relative the outer periphery of the arm base. The second height is less than the first height. The guiding portion further includes a second portion contiguous with the first portion and extending outward from the arm base above the lock surface. The distance between the cam base and the bottom of the second portion is slightly greater than the depth of the mounting rail and the distance between the ends of opposing second portions is less than the height of the mounting rail.

In still another detailed aspect, the first recess includes a top region defined by at least one substantially planar top surface and an arcuate top surface, the arcuate top surface further defining an arcuate top region. The first recess further includes a bottom region defined by at least one substantially planar bottom surface and an arcuate bottom surface, the arcuate bottom surface further defining an arcuate bottom region. The rail cam has a closed/lock position during which the second portion of one of the arms is positioned above the at least one bottom surface and the second portion of the other arm is positioned below the at least one top surface, and the rail cam has an open/release position during which the second portion of one of the arms is positioned below the at least one bottom surface and the second portion of the other arm is positioned above the at least one top surface.

In a second facet, the invention relates to an interface device for securing an instrument to a docking station having a casing having at least one signal port and a mounting rail mounted within a recessed portion of the casing. The interface device includes a back panel forming part of an instrument housing for housing the instrument, a first portion protruding rearward from the back panel and a first recess carried by the protruding portion. The first recess is dimensioned to receive the mounting rail. The interface device further includes a rail cam rotatably mounted within the protruding portion and aligned with the first recess to receive and retain the mounting rail and at least one first-portion signal port carried by the first portion. The first portion is dimensioned to fit within the recessed portion of the casing such that the rail cam is positioned to receive the mounting rail and the at least one first-portion signal port is aligned, in a complementary fashion, with the at least one casing signal port.

In a detailed facet, the interface device further includes a pole clamp assembly positioned near the first and second portions. The pole clamp assembly includes a pivot member moveable between a retracted position and an extended position and a post having an axis. The post is mounted to the pivot member for axial movement and mounted thereto such that when the pivot member is retracted the axis of the post is substantially parallel with the back panel and when the pivot member is extended the axis of the post is substantially perpendicular to the back panel. In another facet, the at least one first-portion electrical port includes a power inlet and the at least one casing electrical port includes a power outlet. In yet another detailed aspect, the casing includes a relay for controlling the application of power to the power outlet when activated and the first portion comprises a magnet positioned such that when the first portion is within the recessed portion of the casing the magnet activates the relay. In further additional aspects, the at least one first-portion electrical port comprises a data communications port, the data communications port comprises an IR port and the casing and first-portion comprise a plurality of complementary signal ports.

In a third aspect, the invention relates to a rail cam forming part of an instrument housing for securing the instrument housing to a mounting rail having a height and depth and mounted to a surface. The rail cam includes a cam base having a surface. The base is mounted for pivotal movement relative the remainder of the instrument housing. The rail cam further includes two opposing arms near the periphery of the cam base. The arms extending substantially perpendicular relative the surface of the cam base, each arm has an arm base defining a lock surface. The arms are positioned on the cam base such that the distance between the two lock surfaces is substantially equal to the height of the mounting rail. The rail cam further includes a guiding portion at the top of each arm base for contacting the mounting rail during insertion of the rail cam onto the mounting rail and transferring the force of contact with the mounting rail to the cam base to therein induce rotation of the rail cam from a closed/lock position to a opened/receive position during which the rail cam receives the mounting rail and subsequently removing the force from the cam base to allow rotation of the rail cam from the open/receive position to the closed/lock position during which the rail cam retains the mounting rail.

In a detailed aspect, the guiding portion includes a first portion sloping downward from a first height near the outer periphery of the arm base to a second height inward relative the outer periphery of the arm base. The second height is less than the first height. The guiding portion further includes a second portion contiguous with the first portion that extends outward from the arm base a distance over the lock surface. The distance between the cam base and the bottom of the second portion is slightly greater than the depth of the mounting rail and the distance between the ends of opposing second portions is less than the height of the mounting rail. In another detailed facet, the rail cam further includes a lever coupled to the rail cam such that movement of the lever induces rotation of the rail cam between the closed/lock position and an opened/release position during which the mounting rail may be removed from the rail cam, the opened/release position being substantially the same as the opened/receive position.

In a fourth facet, the invention relates to a docking station for accepting at least one instrument having a housing having a rail cam and a recess and at least one signal port. The docking station includes a casing having a plurality of fastening bars recessed a distance from the front of the casing, a docking tile secured to the fastening bars and a rail mounted on the docking tile and spaced a distance therefrom. The mounting rail is dimensioned to fit within the housing recess and the rail cam. The docking station further includes at least one signal port secured to the tile. A portion of the port protrudes forward from the tile and is aligned to couple with the at least one housing signal port when the mounting rail is within the housing recess and rail cam. The signal port further includes a portion protruding rearward from the tile for interfacing with a signal source.

In a detailed aspect, the fastening bars comprise channels running the length of the casing and the docking tile may be adjustably positioned along the length of the channels. In another detailed facet, the docking station further includes an electrical circuit mounted to the rear of the docking tile. The electrical circuit provides electrical communication between the at least one tile signal port and an external electrical device. In yet another detailed aspect, a plurality of docking tiles are positioned adjacent each other along the length of the casing. The docking tiles are spaced apart to allow for the mounting of a plurality of instruments having a standard height. In a more detailed aspect, the docking station further includes spacing plates positioned between adjacent docking tiles to thereby provide a docking station capable of accepting instruments of non-standard height. In still another detailed aspect, the docking station further comprises a base tile for providing signals to each of the plurality of docking tiles.

In further additional facets of the docking station, the base tile includes a power inlet for receiving external power to be provided to each of the plurality of docking tiles and the base tile includes a data communication port for interfacing each of the plurality of docking tiles with an external computer system.

In a fifth facet, the invention relates to a docking tile for accepting an instrument having a housing having a rail cam and a recess and at least one electrical port. The docking tile includes a plate, a rail mounted on the plate and spaced a distance therefrom. The rail is dimensioned to fit within the housing recess and the rail cam. The docking tile further includes at least one signal port secured to the plate. A portion of the port protrudes forward therefrom and is aligned to couple with the at least one housing signal port when the rail is within the housing recess and the rail cam. The port further includes a portion protruding rearward therefrom for interfacing with a signal source.

In a detailed aspect, the docking tile further includes an electrical circuit for providing electrical communication between the at least one tile signal port and an external electrical device. In more detailed facets, the at least one tile signal port is a power inlet. In yet another detailed aspect, the electrical circuit includes a magnetic relay for feeding power to the power outlet when activated. In additional facets, the at least one tile electrical port is a data communications port and the data communications port is an IR port.

In a sixth facet, the invention relates to a pole clamp assembly forming part of an instrument housing having a back panel with a pole clamp recess. The pole clamp assembly is for securing the instrument housing to a pole and includes a pivot member moveable between a retracted position and an extended position. The pole clamp assembly further includes a post having an axis. The post is mounted to the pivot member for axial movement and mounted thereto such that when the pivot member is retracted the axis of the post is substantially parallel with the back panel and when the pivot member is extended the axis of the post is substantially perpendicular to the back panel. The post is dimensioned and oriented such that when the pivot member is in the retracted position a portion of the post lies within the pole clamp recess.

In a detailed aspect, the pole clamp recess is defined by a generally arcuate surface and the post includes a threaded stud and a handle having opposing curved sides shaped to substantially match the curved shape of the arcuate surface. The handle is positioned at one end of the stud such that when the pivot member is retracted a portion of the handle lies within the pole clamp recess. In a more detailed aspect, the handle further includes opposing rounded edges, wherein upon the application of force to either of the rounded edges the handle is rotated such that one of the curved sides of the handle generally aligns with the arcuate surface defining the pole clamp recess. In another detailed facet, the pole clamp assembly further includes a bracket mounted to the back panel. The bracket has a stud recess and the pivot member comprises a generally L-shaped arm having a first leg and a second leg. The first leg is mounted to the bracket for pivotal movement and the second leg for accepting the stud. The second leg is positioned relative the first leg to extend into the area near the pole clamp recess such that a portion of the stud lies within the stud recess of the bracket.

In a seventh aspect, the invention relates to a device interface for securing an instrument to a docking station having a casing having a mounting rail mounted within an alignment portion of the casing. The device interface includes an alignment member forming part of an instrument housing for housing the instrument and a rail cam rotatably mounted to the instrument housing and configured to receive and retain the mounting rail. The alignment member interfaces with the alignment portion such that the rail cam is positioned to receive the mounting rail.

In a more detailed facet the alignment portion of the casing includes a recess having a width and the alignment member includes at least one portion protruding from the instrument housing having a width slightly less than the width of the recess.

These and other aspects and advantages of the invention will become apparent from the following detailed description and the accompanying drawings, which illustrate by way of example the features of the invention.

BRIEF DESCRIPTION OF THE DRAWINGS

FIG. 2 is an isometric view of the docking station of FIG. 1 with the medical devices removed and having a casing with a plurality of docking tiles recessed therein and a base tile;

FIG. 3 is an isometric rear view of a medical device having a medical device interface located at the rear of the instrument, the medical device interface having a rail cam assembly, a pole clamp assembly, power connector, IR communications port, and an instrument alignment member;

FIG. 5 is an isometric view of the medical device of FIG. 3 secured to a pole by the pole clamp assembly;

FIG. 10 is an isometric view of a portion of the casing of FIG. 2;

FIG. 11 is a plan view of the casing of FIG. 10;

FIG. 19a is an isometric view of the pole clamp assembly of FIG. 3 in an opened position;

FIG. 19b is an isometric view of the pole clamp assembly of FIG. 3 in a closed position;

FIG. 19c is a top view of the pole clamp assembly of FIG. 19a; and

FIG. 19d is a top view of the pole clamp assembly of FIG. 19b.

DETAILED DESCRIPTION OF PREFERRED EMBODIMENTS

Figure 1:
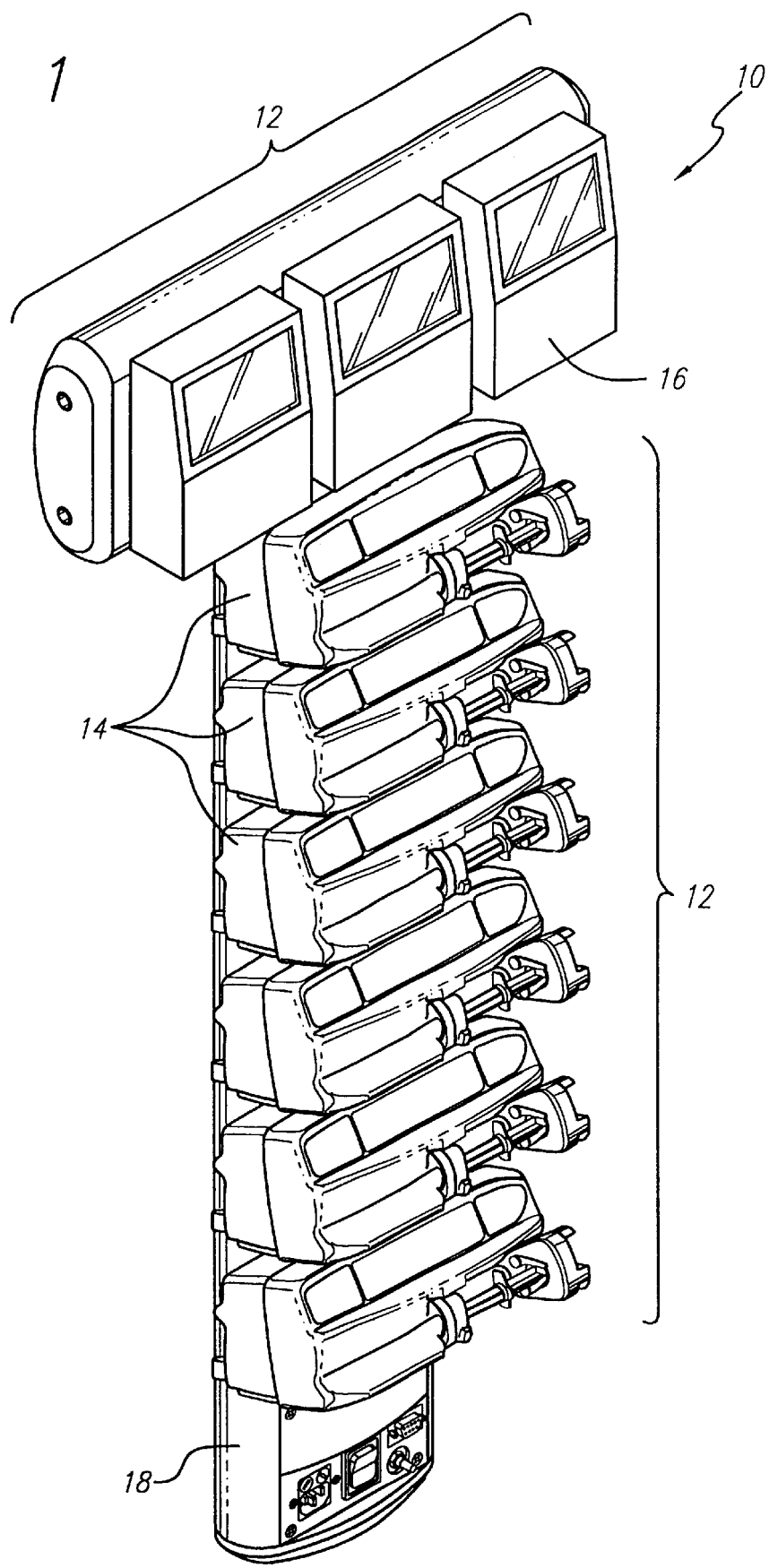
FIG. 1 is an isometric view of a medical interface system in accordance with the invention showing a plurality of medical devices, each of which is secured to a docking station by a medical device interface.

Turning now to the drawings, in which like reference numerals are used to designate like or corresponding elements among the several figures, in FIGS. 1–3 there is shown a medical device interface system 10 (FIG. 1) used with a plurality of individual medical devices 12, such as syringe infusion pumps 14 and peristaltic infusion pumps 16. Other types of medical devices not shown in FIG. 1 may be incorporated into the system. Such as blood pressure and oxygen monitoring devices. Each of the medical devices 12 is removably secured to a docking station 18 (FIG. 2) by a medical device interface 48 (FIG. 3) located at the rear of each device.

The docking station 18, as shown in FIG. 2, includes a plurality of docking tiles 20 and a base tile 22, each mounted to a casing 24. Each docking tile 20 includes a mounting rail 26 mounted to a plate 28. The mounting rail 26 has standard height and depth dimensions. Also mounted to the plate 28 are a power outlet 30 and a data communications port 32 for interfacing with complementary power and data communications components located on the rear of the medical devices 12 (FIG. 3). The docking tiles 20 include a fastener 34 in each corner of the plate 28 for mounting the docking tile to the casing 24.

The base tile 22 includes a main power inlet 36 and a main on/off switch 38 for connecting each of the docking tiles 20 with an external power source. In some embodiments, the base tile 22 further includes a data communications port 40 for connecting each of the docking tiles 20 with an external data communications device, such as a computer. The base tile 22 is secured to the casing 24 via front panel fasteners 42. The inside region of the casing 24 and the docking tile plate 28 are dimensioned such that the plate fits within the casing.

With reference to FIG. 3, a medical device interface (MDI) 48 which in this case forms part of a medical device 12 housing is located at the rear of the device. The mounting case 50 of the instrument has a back panel 76 on which is located the MDI 48. The MDI includes an instrument alignment mounting member 51, the purpose of which is to automatically align the other components of the MDI with complementary components of the docking station or of another station. In this embodiment, the instrument alignment mounting member 51 has a first portion 52 and a second portion 54, each protruding rearward from the back panel. The first protruding portion 52 includes a first recess 56 while the second protruding portion 54 includes second recess 58. Each recess 56, 58 is dimensioned to receive the mounting rail 26 (FIG. 2) of a docking tile 20.

The MDI 48 (FIG. 3) further includes a rail cam 60 that is positioned within the first recess 56 and mounted therein for rotation. The rail cam 60 is biased to a closed/lock position. The rail cam 60 includes two opposing arms 62, each having a base 78 and a guiding portion 64 on top of the base. Each guiding portion 64 has a sloping surface having a portion 80 that extends out over the base 78 of the arm. The arm bases 78 are spaced apart a distance slightly greater than the height of a mounting rail, such that the mounting rail fits between the arms. The space between the tips of the extension portions 80 is less than the height of the mounting rail.

The guiding portion 64 is sloped to receive the force of a mounting rail 26 during mounting and to induce rotation of the rail cam 60 against its spring bias to an open/receive position during which the mounting rail slips into the space between the arm bases 80. Once the mounting rail 26 is positioned within the rail cam 60, the rail cam rotates back to its closed/lock position. In the closed/lock position of the rail cam 60, the extension portions 80 of the arms 78 are located behind the mounting rail 26, thereby retaining the mounting rail within the rail cam and the first and second recesses 56, 58.

The MDI 48 also includes a lever 66 positioned at the top of the mounting case 50. The lever 66 rotates the rail cam 60 from its closed/lock position against its spring bias to an open/release position during which the medical device 12 may be removed from the mounting rail 26. The open/release position and the open/receive position are identical. This position is sometimes referred to as the open/receive/release position. The MDI 48 further includes a power inlet 68 and a data communication port 70 which are aligned to communicate with complementary power and data communications components located on the docking tiles 20 (FIG. 2).

Also included in the MDI 48 is a pole clamp assembly 72 which may be extended for purposes of securing the medical device 12 to a pole. The pole clamp assembly 72 includes an arm 82 and a threaded post 84. The arm 82 is pivotally mounted to the back panel 76 and moves between open and closed positions. The post 84 is attached to the arm 82 and threadably mounted thereto for movement along the axis of the post. The pole clamp assembly 72 is positioned relative the first and second portions 52 and 54 such that when the pole clamp assembly is closed the post 84 is positioned in a recess between the two portions. When the pole clamp assembly 72 is opened, the post 84 is substantially perpendicular to the back panel 76. In this position, the post 84 may be rotated to tighten against a pole placed between the tip of the post and the back panel 76.

Figure 4A:
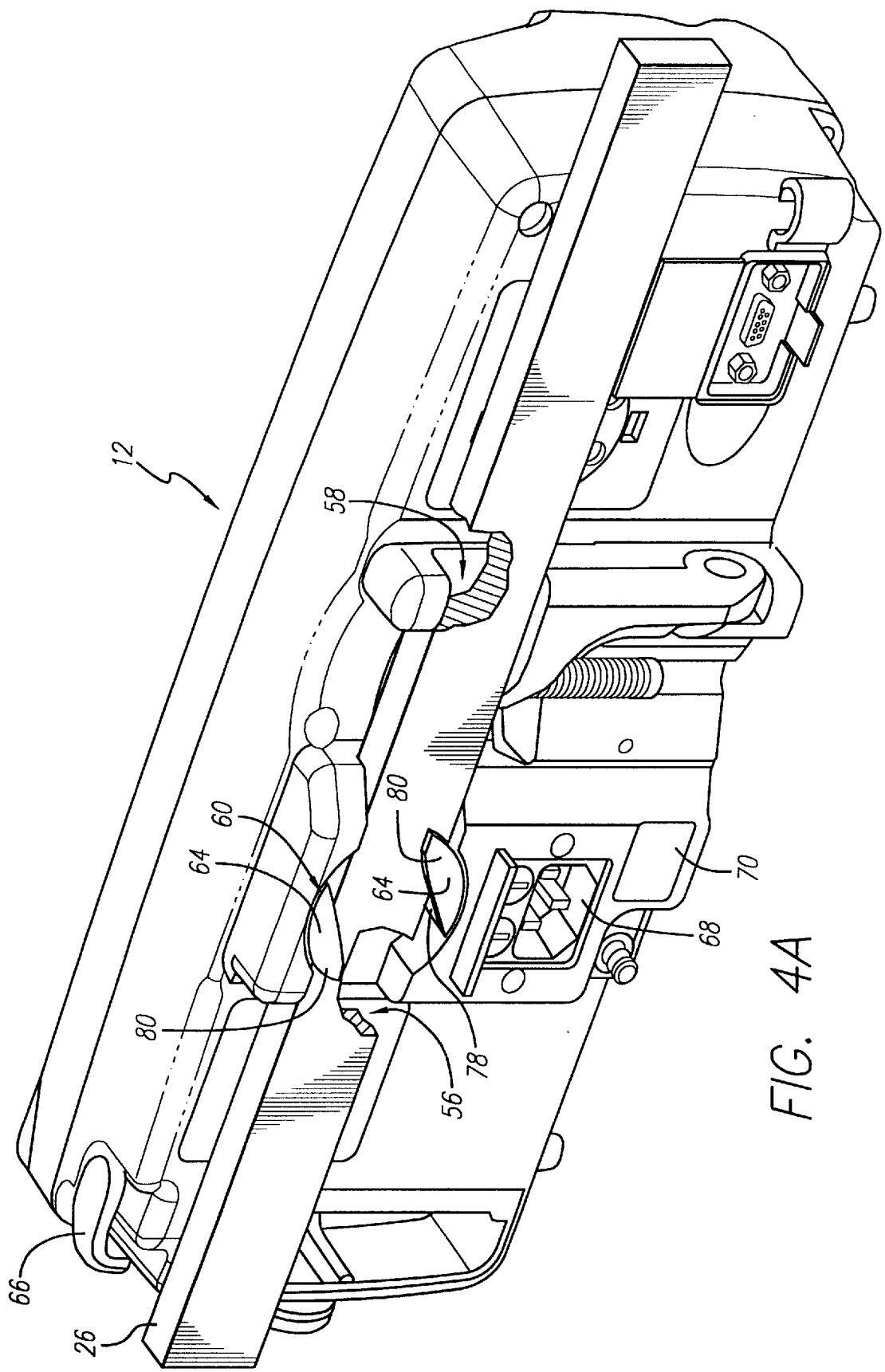
FIG. 4a is an isometric view of the medical device of FIG. 3 secured to a mounting rail by the rail cam assembly with portions of the rail cut away for clarity.
Figure 4B:
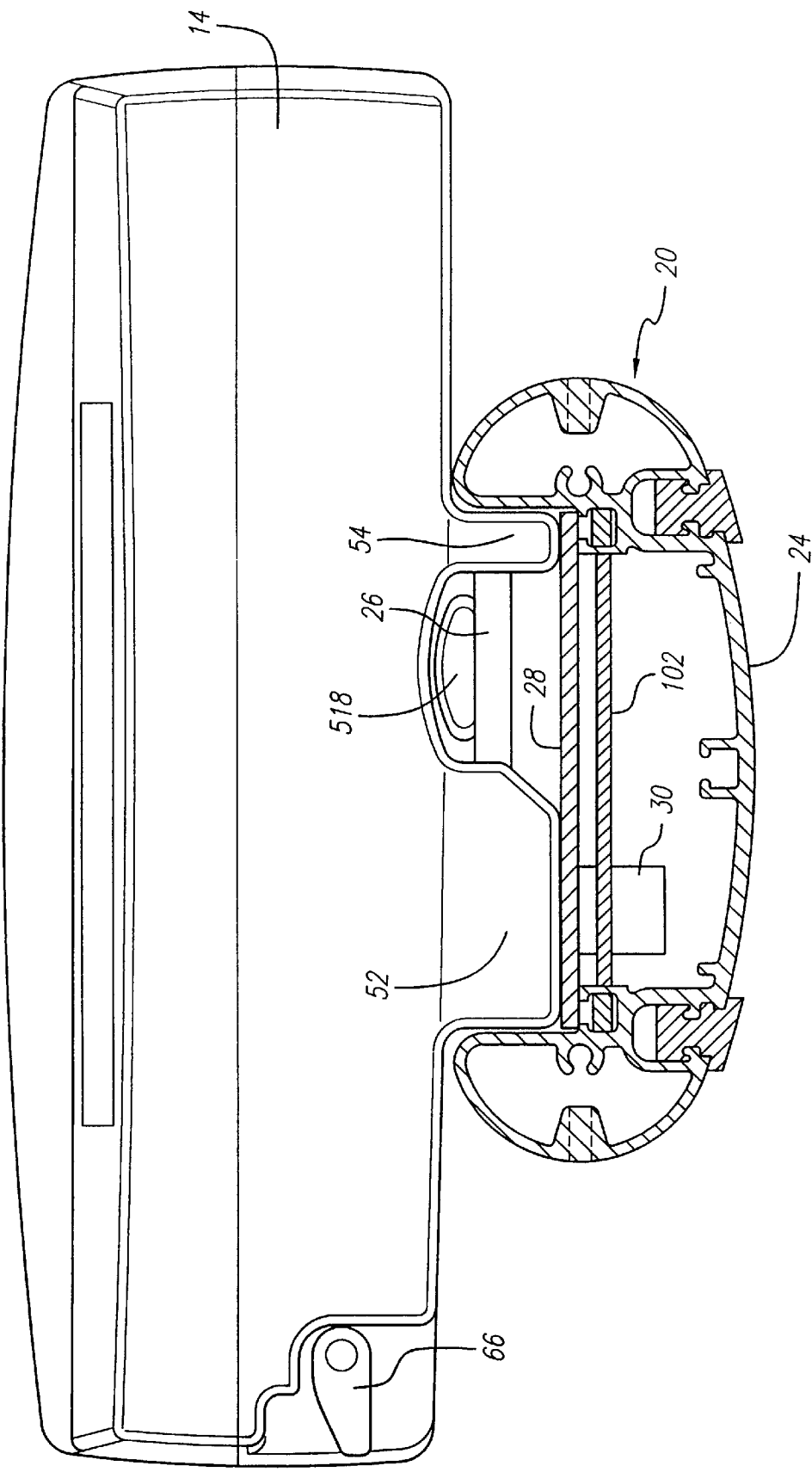
FIG. 4b is a plan view of the operation of the alignment mounting member at the back of the medical device of FIG. 3 interacting with the alignment recess of the docking station casing to properly and automatically align the power and communications devices of the instrument with those of the docking tile.

In operation, as shown in FIG. 4a, a medical device 12 is secured to a mounting rail 26 by visually aligning the first recess 56 and the second recess 58 with the mounting rail. Once aligned, the rail cam 60 is pushed against the mounting rail 26. The force of the mounting rail 26 against the guiding portions 64 of the rail cam 60 induces rotation of the rail cam such that the mounting rail slides into the space between the arm bases 78. Once the mounting rail 26 is positioned within the rail cam 60, the cam returns to its closed/lock position and the extension portions 80 of the arms 62 hold the device 12 to the rail. If the mounting rail 26 is part of a docking station 18 (FIG. 2), the power inlet 68 (FIG. 4) of the medical device 12 and the power outlet 30 (FIG. 2) of the docking tile 20 interconnect. Likewise, the data communications ports 32, 70 of the two structures interface. To remove the medical device 12 from the rail cam, the lever 66 is activated to cause the rail cam to rotate to its open/release position during which time the extension portions 80 no longer retain the device to the mounting rail 26. Likewise, as shown in FIG. 4b, a medical device 12 is secured to a docking tile 20 by visually aligning the alignment mounting member 51 of the device with the recess formed by the casing 24. Once aligned, the rail cam 60 is pushed against the mounting rail 26 and secured thereto as just described with reference to FIG. 4a.

Alternatively, as shown in FIG. 5, the medical device 12 may be mounted to a pole 74 using the pole clamp assembly 72. In order to do so, the arm 82 of the pole clamp assembly 72 is pivoted to its open position. The medical device 12 is placed on the pole 74 such that the pole lies in the area between the first and second portions 52, 54 of the MDI 48. The threaded post 84 is then rotated until the tip of the post contacts the pole, thereby clamping the instrument 12 to the pole 74.

Following are further detailed descriptions of the docking station 18 (FIG. 2) and medical interface device 48 (FIG. 3).

Docking Station

As previously mentioned with reference to FIG. 2, the docking station 18 includes a plurality of docking tiles 20 and a base tile 22, each mounted to a casing 24. The base tile 22 is typically positioned near the bottom of the docking station to provide for easy connection with power and data communications cables. The docking tiles 20 are positioned adjacent each other, one on top of the other or in a side-by-side arrangement. The docking tile 20 are dimensioned such that when assembled they are spaced apart a distance sufficient to accept a medical device 12 of standard height and/or width dimensions. Tile spacers (not shown) may be positioned between adjacent docking tiles 20 in order to increase the distance there between to allow for acceptance of non-standard dimensioned medical devices 12 without physical interference between the devices. The docking station 18 may either be a "dumb" station, i.e., one which provides only power to the medical devices 12, or a "smart" station, i.e., one which provides both power and data communications to the medical devices. In the embodiment shown in FIG. 2, the docking station 18 includes a vertical casing 44 and a horizontal casing 46. The casings 44, 46 are joined together by a T-piece 47 that fits within the top of the vertical casing 44 and is fastened to the back of the horizontal casing 46. At each end of the horizontal casing 46 is a removable end cap 49.

Figure 6:
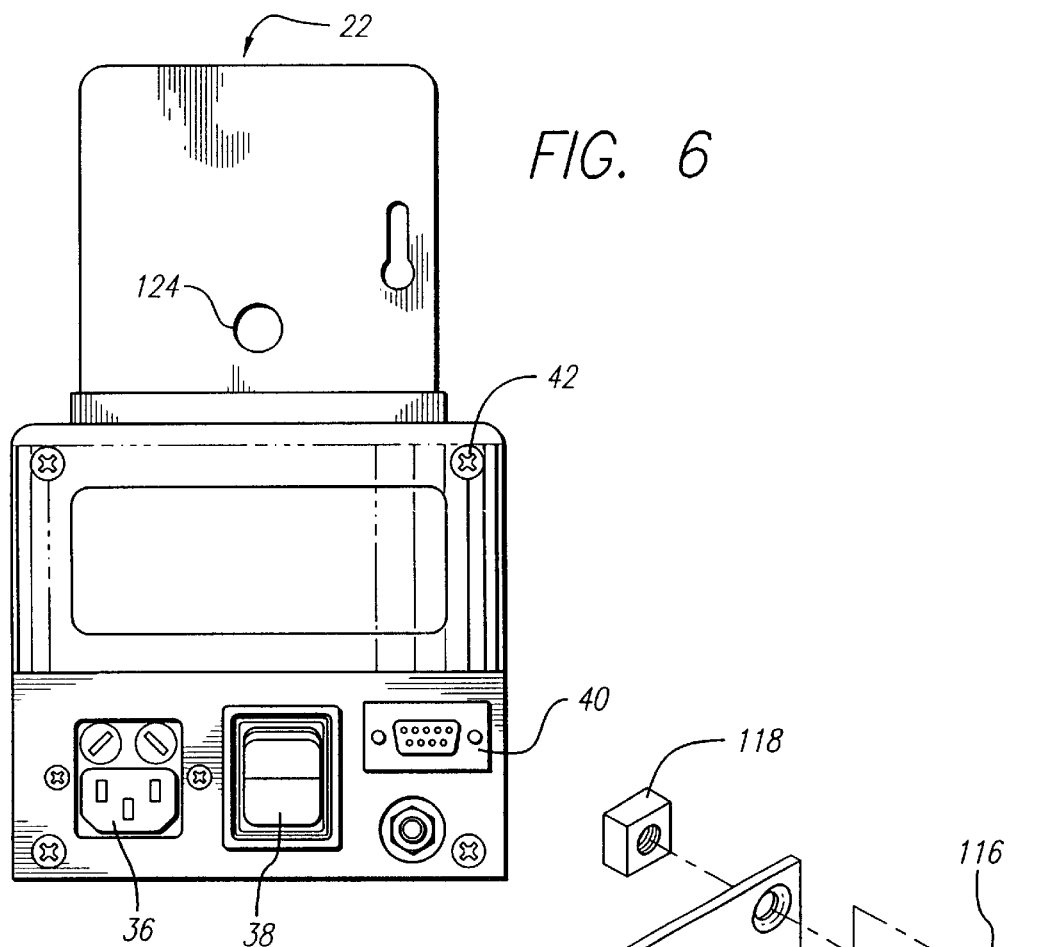
FIG. 6 is a front view of the base tile of FIG. 2.

As shown in FIG. 6, the base tile 22 includes a main power inlet 36 and an on/off switch 38 for interfacing each of the docking tiles 20 with an external power source. Power is provided to each docking tile 20 in a daisy chain manner through connection provided by adjacent tiles, as described further below. The base tile 22 includes a connection port through which an earth connection is made with the back of the casing 24. In a smart docking station, the base tile 22 further includes a data communications port 40 for interfacing each of the docking tiles 20 with an external data communications device, such as a computer. The base tile 22 coordinates data communications with all individual docking tiles 20 located in the docking station. Such communications may take the form of a central hospital computer monitoring the status or location, or both, of an individual medical device mounted at the docking station. In a preferred embodiment, the base tile 22 includes Ethernet circuitry for interfacing with an Ethernet system. Alternatively, the base tile 22 may include the necessary interface for communicating with other devices through an RS-232 bus or other similar bus configurations.

Figure 7:
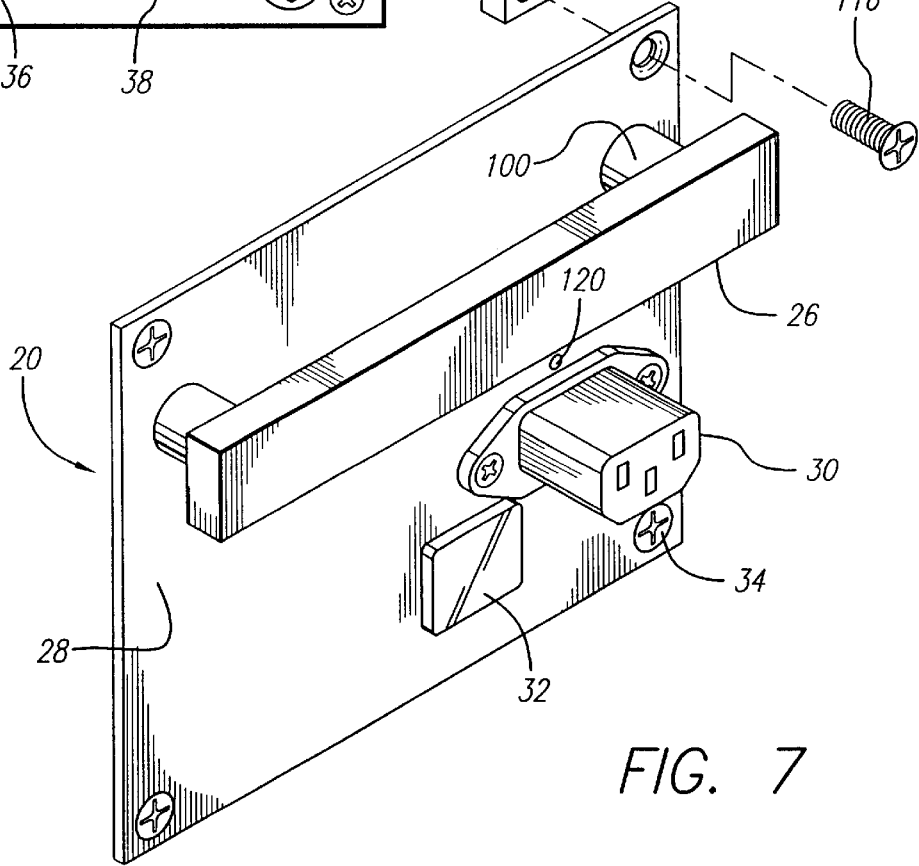
FIG. 7 is an isometric view of one of the docking tiles of FIG. 2.
Figure 8:
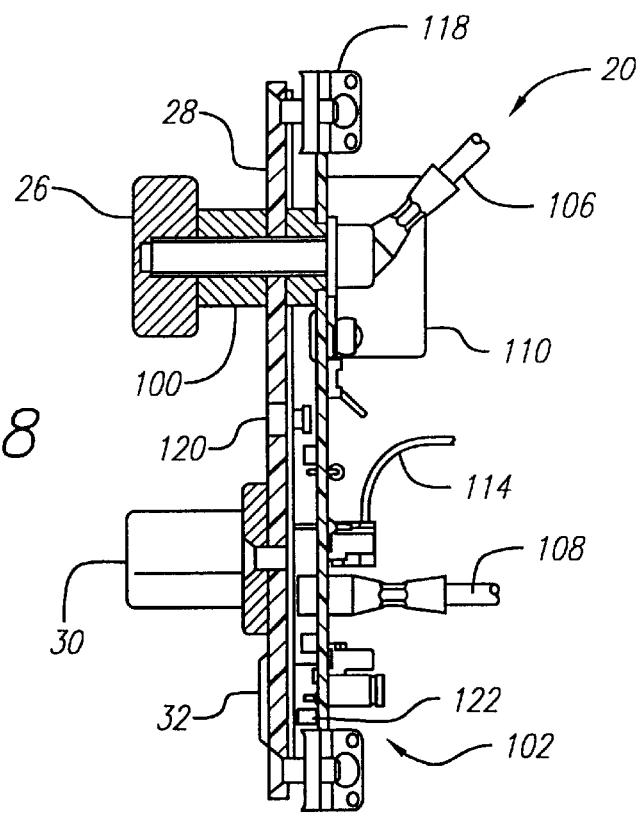
FIG. 8 is a side view of the docking tile of FIG. 7 showing a mounting rail, power connector, signal ports and a circuit card mounted to the back of the tile.
Figure 9:
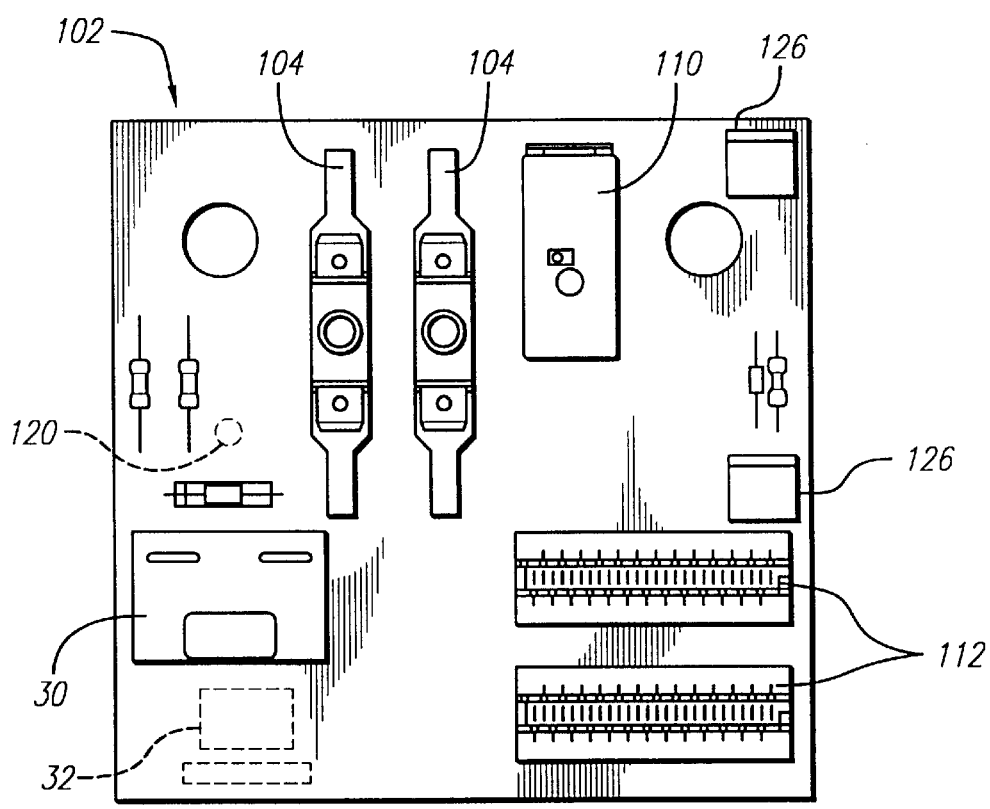
FIG. 9 is a diagram of the circuit card of FIG. 8.

As shown in FIGS. 7–9, each docking tile 20 includes a standard size mounting rail 26 mounted to a symmetrical shaped plate 28. In a preferred embodiment, the plate 28 is square, although other shapes are possible, such circular. The mounting rail 26 has a standard height and depth. In a preferred embodiment, the mounting rail 26 has a height of approximately 25 mm and a depth of approximately 10 mm. The mounting rail 26 is spaced a distance from the plate 28 by a plurality of spacers 100. The spacers 100 are dimensioned to position the mounting rail 26, relative the plate 28, such that during mounting, the plate does not contact the back surface of the first and second portions 52, 54 (FIG. 3). The spacers 100 thus ensure that the plate 28 does not inhibit movement of the mounting rail 26 into the first and second recesses 56, 58 and the rail cam 60.

Also mounted to the plate 28 (FIG. 7) are a plurality of signal ports, e.g., power outlet 30 and a data communications port 32. The power outlet 30 is positioned on the plate 28 to align with a complementary power inlet 68 (FIG. 3) located on the rear of a medical device. During installation of a medical device 12 to a docking tile 20 (FIG. 7), the complementary power components interconnect. Likewise, the data communications port 32 is positioned on the plate 28 to align with a complementary data communications component 70 (FIG. 3) located on the rear of a medical device 12. In a preferred embodiment, the complementary data communication components are infrared ("IR") ports. Alternatively, the communications components may be mechanical in nature, such as pin connectors or telephone connectors.

A circuit card 102, as shown in FIGS. 8 and 9, is mounted on the rear of the plate 28. The circuit card 102 carries a plurality of circuit components for connecting the signal ports 30, 32 of individual docking tiles 20 to the corresponding signal ports on the base tile 22. With regard to power connections, each docking tile 20 receives power through the base tile 22.

Power lugs 104 located on the circuit card receive power from the base-tile power source via power cables 106. Adjacent docking tiles 20 are interconnected in a daisy chain manner through the power cables 106. This power is provided to the power inlet 30 via relay 110. A cable 108 provides an earth connection to the casing 24 (FIG. 2). The circuit card 102 also includes a relay 110 that is activated by a magnet 342 (FIG. 17) positioned within the medical device. When the medical device 12 is mounted on the docking tile 20, the magnet 342 activates a reed switch 122 which activates the relay 110 to allow for the application of power through the power outlet 30. Activation of the relay 110 is indicated by illumination of a red LED 120 located on the circuit board 102 and visible at the front of the docking tile 20 (FIG. 7). The LED 120 illuminates when the relay is activated. The relay 110 acts as a safety feature by blocking the power signal from the power outlet 30 in the absence of a medical device. Should the relay 110 fail and stick in the activated position, even upon removal of the medical device 12 from the docking tile 20, the LED 120 indicates the presence of power at the outlet 30.

In a dumb docking station, the relay 110 is powered by a 12 volt dc signal provided by power connectors 126. These power connectors 126 receive power from the base tile 22. The power signal is passed through adjacent docking tiles 20 in a daisy chain manner. In a smart docking station the circuit card 102 further includes data communication connectors 112. These connectors 112 provide the dc power signal to power the relay 110. These connectors 112 also communicate with a data cable 114 to provide an interface between the IR port 32 and the main data communications port 40 of the base tile 22. Adjacent docking tiles 20 are daisy chained together via connectors 112 to provide communication between each docking tile and the communications device connected to the base tile 22.

Each docking tile 20 is individually mounted to the docking station casing 24 (FIG. 2) by fasteners 34 located in each corner of the plate 28. Each fastener 34 includes a screw 116 and a square nut 118. The square nut 118 fits within the a square fastener channel located in the casing 24, as described further below.

Docking tiles 20 may also be mounted directly to a wall or bed instead of being included as part of a docking station 18. When mounted as such, power and data communications are typically provided directly to the tile, instead of through a base tile 22. Power may be provided by a wall outlet while data communications may be provided by a data cable such as an RS-323 cable or a telephone line.

As shown in FIGS. 10 and 11, the docking station casing 24 includes two sides 200. In a preferred embodiment, the casing 24 is formed of aluminum. This provides structural rigidity to the casing and electromagnetic capability (EMC) shielding, e.g., electromagnetic interference (EMI) protection, as well as weight reduction. The casing may, however, be made of a non-metallic material and EMI screening mounted to the inside to result in the same level of EMI protection as if the casing were made of metal. Each side 200 is substantially semi-circular in shape and is hollow along its entire length. These hollow sides 200 provide rigidity to the casing 24 while at the same time reducing the weight. An arced back panel 202 joins the two sides 200. At the junctions 204 of the back panel 202 and side 200 is a rear channel bar 206 that runs the entire length of the casing 24. Inserted within each of the rear channel bars 206 is a channel plug strip 208 (FIG. 11). The channel plug strips 208, which may be formed of rubber, may be removed and a bracket (not shown) may be installed across the rear of the casing 24 for mounting the casing to a wall or other support medium.

On the inside of the casing 24 is a center channel bar 210. The center channel bar 210 receives the earth cable 108 (FIG. 8) and thereby provides earth bonding. Also on the inside of the casing 24, near each of the sides 200 is a recess channel bar 212 that runs the entire length of the casing 24. The recess channel bars 212 are rectangular in cross section and are sized to receive the square nuts 118 (FIG. 7) associated with the docking-tile fasteners 34, as previously described. The casing 24 also includes a pair of threaded channels 222 which receive screws 224 (FIG. 2) for securing the end cap 49 to the casing.

The distance between the inner walls 214 of the sides 200 is selected to be slightly greater than the width of a docking tile plate 28 (FIG. 7) so that the tile can be mounted in the recess 215 formed between the sides 200. The distance between the front of the recess channels 212 and the front 216 of the casing, i.e., the docking station depth, is selected to be slightly greater than the dimension by which the first and second portions 52, 54 (FIG. 3) of the alignment mounting member 51 of the MDI 48 protrude from the back panel 76. The recess 215 between the sides 200 therefore forms an alignment mounting recess that functions to automatically guide the alignment mounting member 51 (FIG. 3) of the medical device 12 into proper alignment with the interface components of the plate mounted in the recess, such as power, data communications, and the mounting rail. The curved configuration of the front 216 part of the casing assists in correctly and automatically aligning the components of the instrument with the components of the docking tile 20 as the interface 48 of the instrument is pressed into the recess 215. This curved configuration tends to direct the interface 48 of the instrument into the recess 215.

Figure 12:
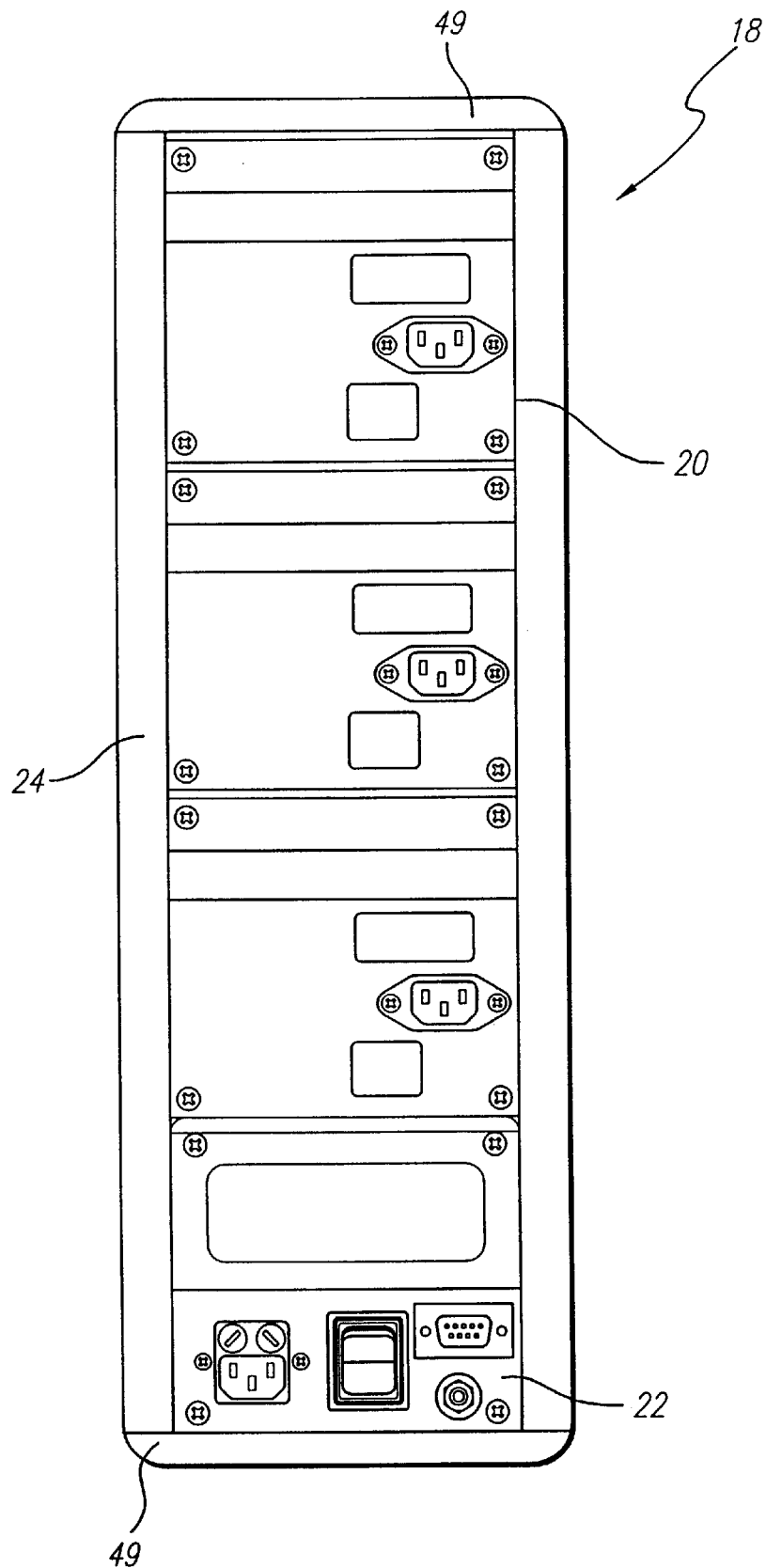
FIG. 12 depicts an alternate configuration of a docking station showing three docking tiles and a base tile.
Figure 13:
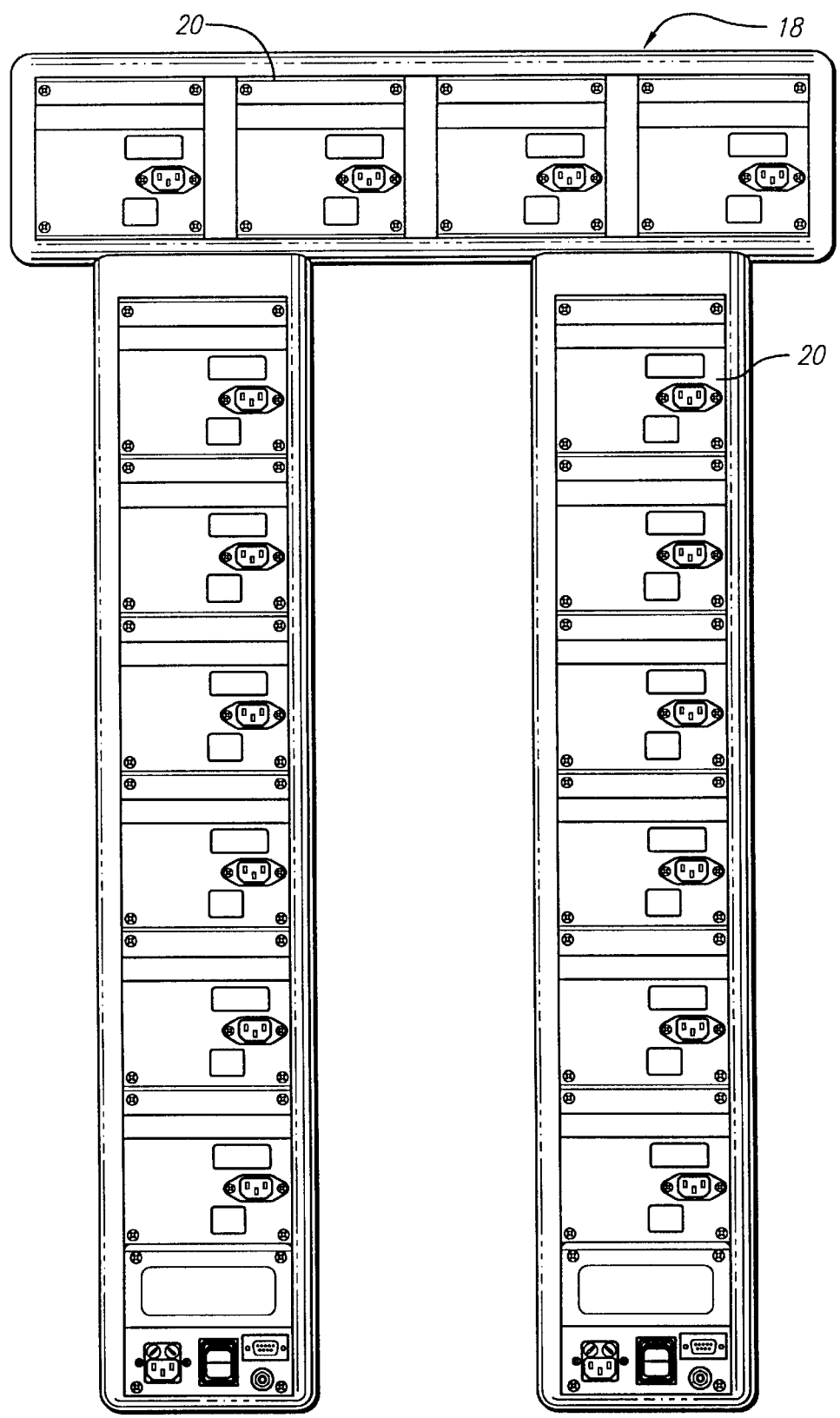
FIG. 13 depicts another alternate configuration of a docking station showing two vertical casings and an interconnecting horizontal casing located at and engaged with the tops of the vertical casings.
Figure 14:
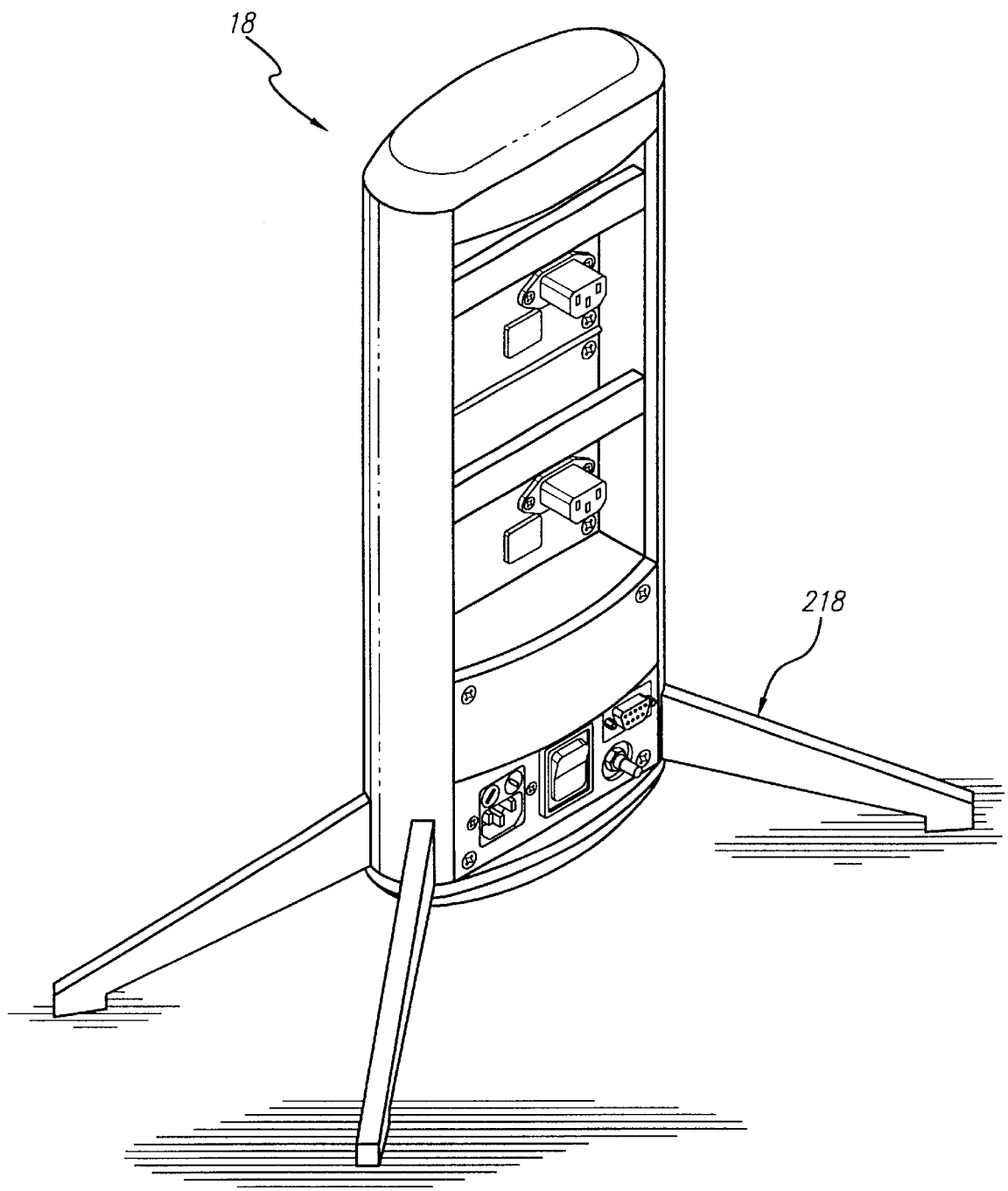
FIG. 14 depicts another alternate configuration of a docking station having a stand.

While the foregoing description of a docking station 18 has been made with reference to the configuration shown in FIG. 2, alternate configurations may be assembled. Examples of alternate configurations are shown in FIGS. 12–14. FIG. 12 shows a docking station having three docking tiles 20 and a single base tile 22 mounted within a casing 24. The casing 24 is capped at the top and bottom and with such a configuration, the entire assembly is particularly suited to be mounted to a wall by means of a mounting bracket inserted in the rear channel bars 206 of the casing (see FIG. 11). With specific reference to FIG. 13, it is noted that the top horizontal portion of the docking station 18 includes the same casing as the vertical portions. During assembly, docking tiles 20 are simply rotated and secured to the casing side-by-side. This is possible due to the square dimensions of the docking tiles plates 28.

Figure 15:
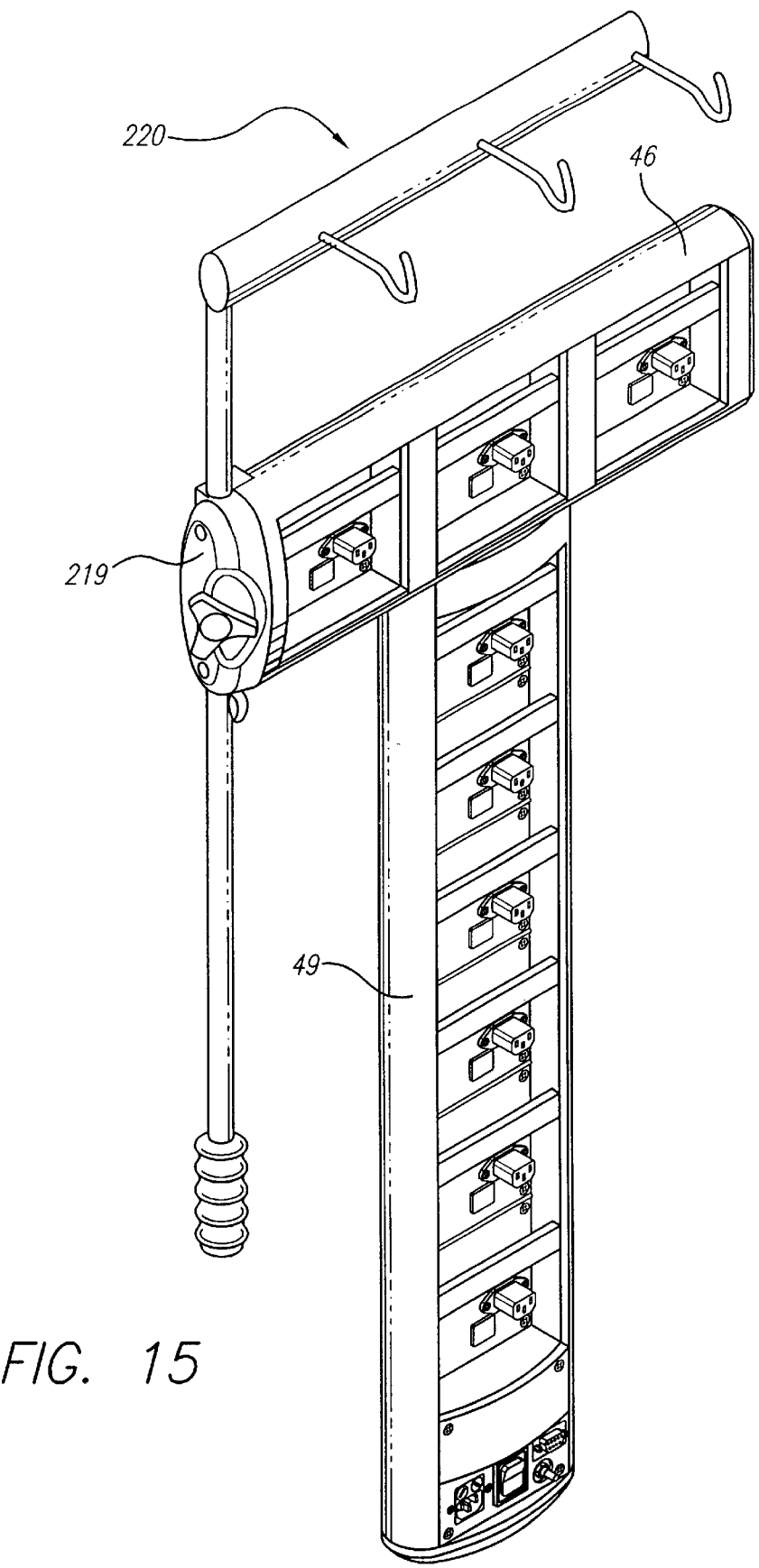
FIG. 15 depicts a docking station having a bag support for holding infusion fluid for use by one or more medical devices that may be mounted to the docking station.

As previously mentioned, docking stations 18 may be mounted to the wall using brackets attached to the back of the casing. Alternatively, a docking station 18 may include a stand 218, as shown in FIG. 14, which allows for placement of the docking station at a location distant from a wall. The stand shown in FIG. 14 can have wheels mounted at the bottom of each foot so that the stand can accompany a patient who is being moved. The medical devices mounted in the docking station 18 include battery backup power that allows the devices to continue operation during movement. As shown in FIG. 15, a docking station may also include accessories such as a hook apparatus 220 for hanging bags of infusion fluid. A clamp assembly 219 in this arrangement is mounted to the end of the horizontal casing 46 instead of an end cap 49 (FIG. 2). The clamp assembly 219 permits control over the height of the hook apparatus 220.

Medical Device Interface

Figure 16:
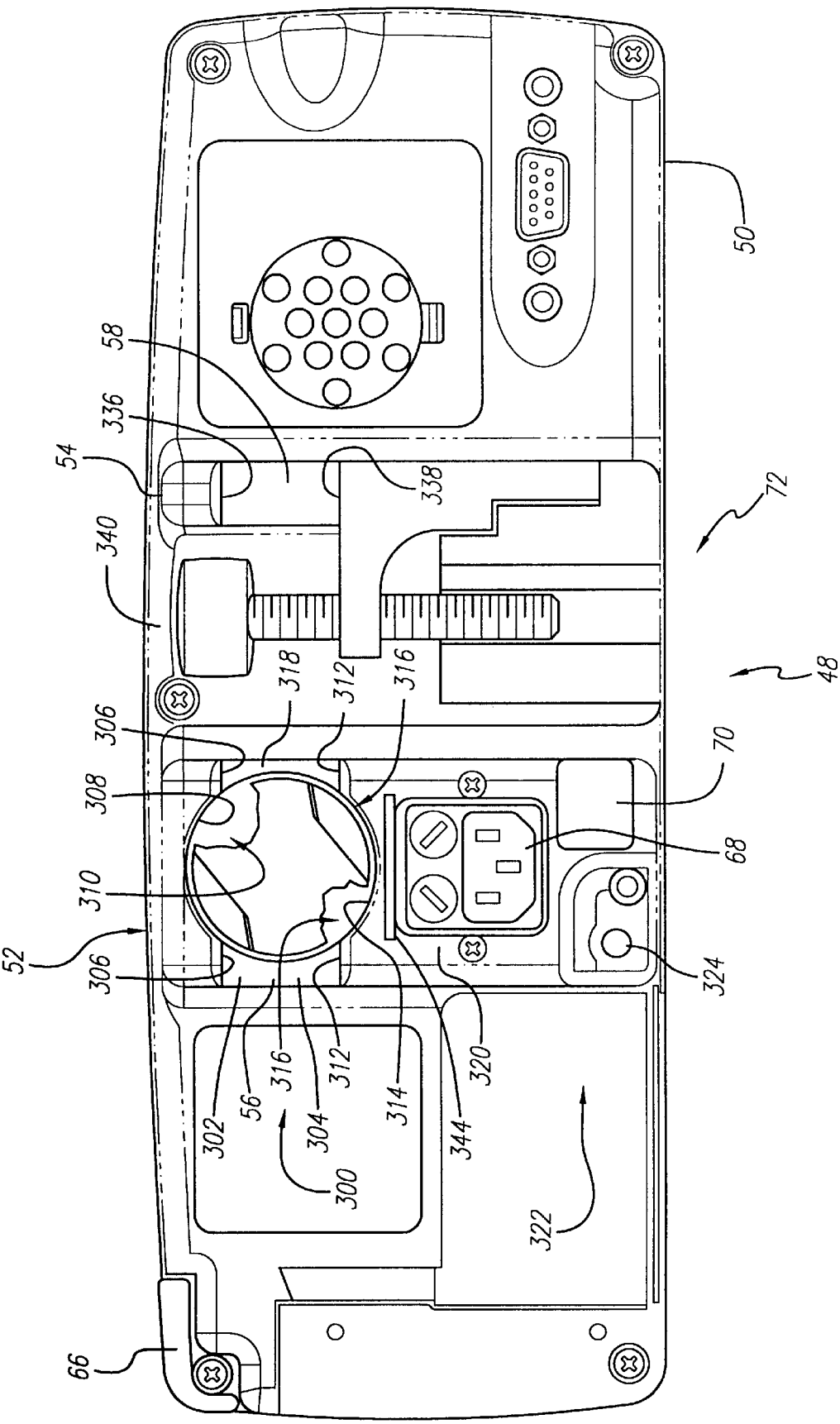
FIG. 16 is a view of the medical device interface of FIG. 3 as viewed from the outside of the medical device with portions of the rail cam cut away for clarity.
Figure 17:
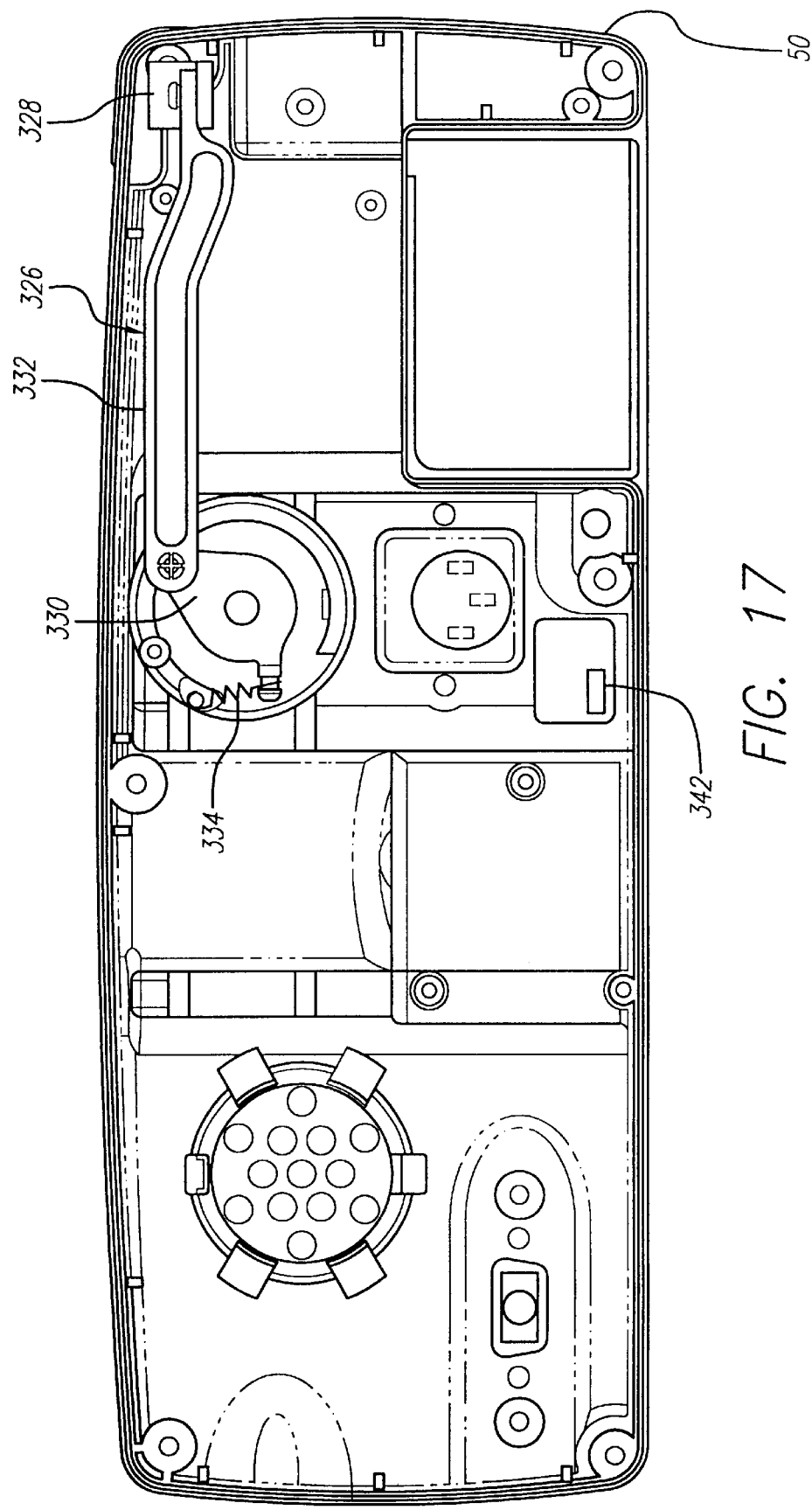
FIG. 17 is a view of the medical device interface of FIG. 3 as viewed from the inside of the medical device showing interconnection of the rail cam to an externally located cam control lever, and also showing the spring bias on the rail cam.

As previously mentioned with reference to FIG. 3, a medical device interface (MDI) 48 forming part of a medical device housing or attached to the housing is located at the rear of the device. The MDI is usually made of plastic. The MDI 48 includes a rail cam 60 and pole clamp assembly 72. With reference to FIGS. 3, 16 and 17, the instrument alignment mounting member 51 forming part of the mounting case 50 has a first portion 52 protruding rearward from the case a distance no greater than the depth of a docking station 20. The first portion 52 has a height no greater than the height of a docking tile 20 and a width no greater than the width of a docking tile.

In the upper region 300 of the first portion 52, is a first recess 56. The first recess 56 includes a top region 302 and a bottom region 304. The top region 302 is defined by two substantially planar top surfaces 306 and an arcuate top surface 308. The portion of the first recess 56 bounded by the arcuate top surface 308 defines an arcuate top region 310. Likewise, the bottom region 304 is defined by two substantially planar bottom surfaces 312 and an arcuate bottom surface 314. The portion of the first recess 56 bounded by the arcuate bottom surface 314 defines an arcuate bottom region 316. The top and bottom planar surfaces 306, 312 are substantially parallel to each other.

The first recess 56 has a height defined by the distance between the top and bottom planar surfaces 306, 312. The height is slightly greater than the height of a mounting rail 26. The first recess 56 has a depth defined by the distance between the back surface 318 (FIG. 3) of the recess and the surface 320 of the first portion. The depth is greater than the depth of a mounting rail 26. Given the height and depth of the first recess 56, when a mounting rail is placed within the first recess and positioned flush against the back surface 318 of the recess, the mounting rail is recessed relative the surface 320 of the first portion.

At the surface 320 of the first portion 52, in the lower region 322, is a power inlet 68, data communications port 70 and a potential equalization connector 324. The power inlet 68 and the data communication port 70 are positioned on the surface 320 of the first portion, relative the first recess 56, such that they align with and interface with the power outlet 30 (FIG. 2) and data communication port 32 of a docking tile when the mounting rail of the docking tile is placed within the first recess. A roof 344, positioned above the power inlet 68, serves to prevents fluid from entering the power inlet so that when the medical device 12 is used in a stand alone configuration, i.e., not with a docking station, it reduces the risk of shorting out the electrical power.

The back surface 318 of the first recess 56 includes a circular cutout positioned such that the top and bottom portions of the cutout align with the top and bottom arcuate surfaces 308, 314. Positioned within the circular cutout is a rail cam 60. As shown in FIGS. 18a–18e, the rail cam 60 includes a circular cam base 400 that fits within the circular cutout such that the surface 402 of the circular cam base is substantially subflush with the back surface 318 of the first recess 56. By "subflush" it is meant that the cam base 402 is positioned a slight distance below the back surface 318. This ensures that the mounting rail 26 contacts the back surface 318 rather than the face of the cam base 402, thereby allowing the rail cam 60 to rotate freely into the closed/locked position without encountering any friction contact with the mounting rail 26. The cam base 400 is mounted for pivotal movement within the cutout. Positioned near the periphery of the cam base 400 and projecting substantially perpendicular relative the surface 402 of the cam base are a pair of opposing arms 62.

Each arm 62 includes an arm base 404 defining a lock surface 406. The arms 62 are positioned on the cam base 400 such that the distance between the two opposite lock surfaces 406 is slightly greater than the height of a mounting rail 26 to allow for placement of the mounting rail between the lock surfaces. Each arm 62 also defines a release surface 412. Each arm 62 further includes a guiding portion 64 located at the top of the arm base 404. The guiding portion 64 includes a first portion 408 sloping downward from a first height near the outer periphery of the arm base 404 to a second height inward relative the outer periphery of the arm base. The second height is less than the first height.

Figure 18A:
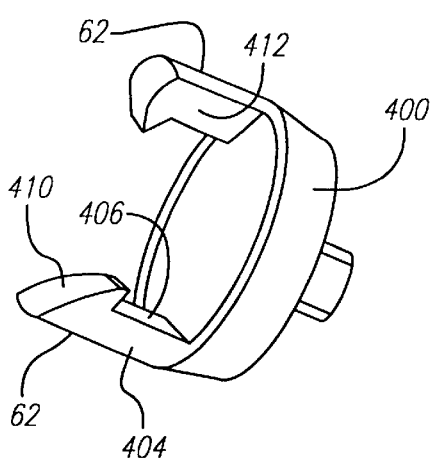
FIGS. 18a and 18b are isometric views of the rail cam of FIG. 3.
Figure 18B:
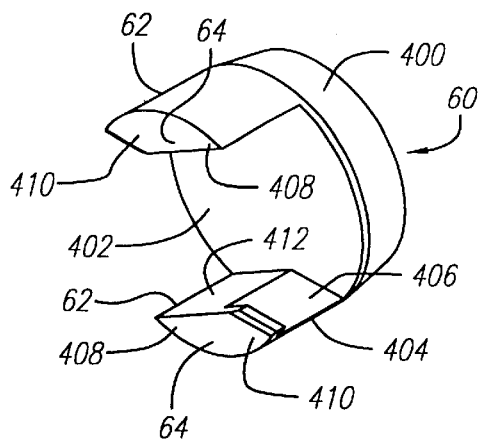
Figure 18C:
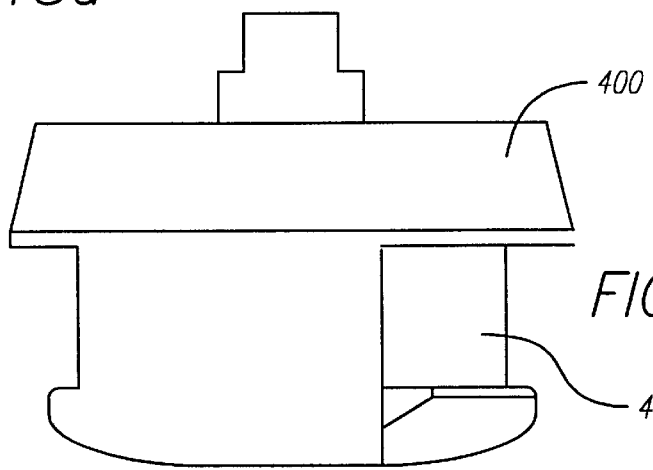
FIGS. 18c through 18e are a plan view, a front view and a side view, respectively, of the rail cam of FIGS. 18a and 18b.
Figure 18D:
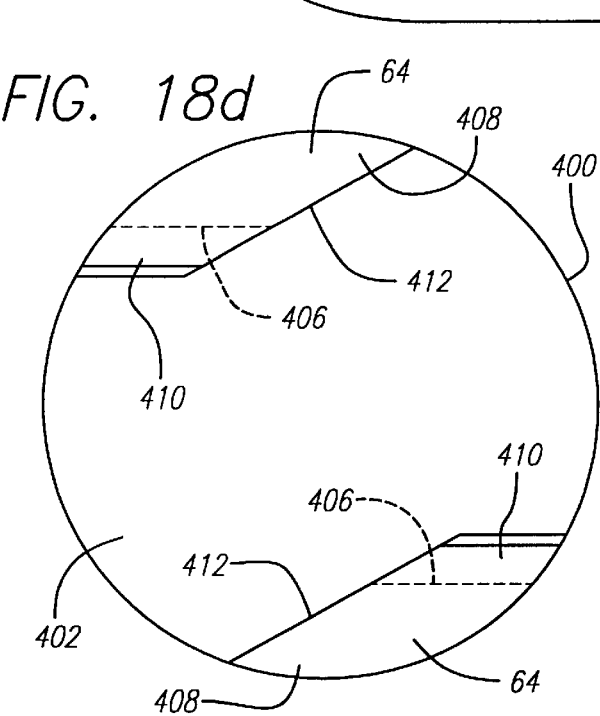
Figure 18E:
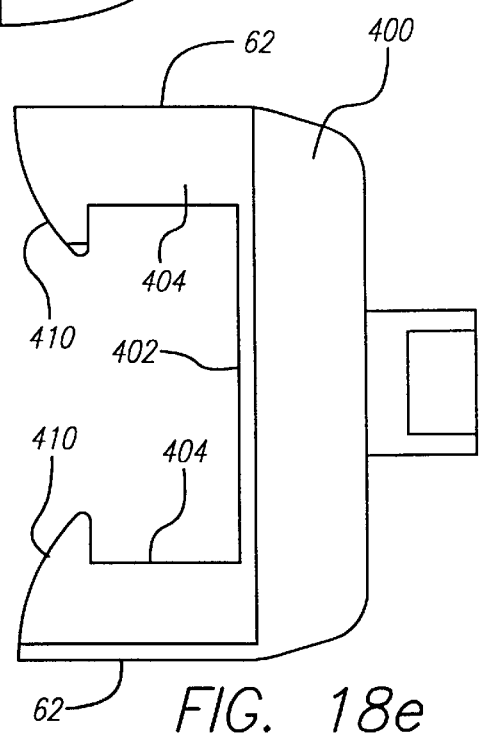

The guiding portion 64 further includes a second portion 410 that is contiguous with the first portion 408. The second portion 410 extends outward from the arm base 404 above the lock surface 406 and acts a lip for retaining a mounting rail 26. The arms 62 are dimensioned such that the distance between the surface 402 of the cam base 400 and the bottom of the second portion 410 as best shown in FIG. 18e is substantially equal to the depth of the mounting rail 26 and the distance between the ends of opposing second portions 410 as best shown in FIG. 18a, is less than the height of the mounting rail. Accordingly, the mounting rail 26 fits within the rail cam 60 and is retained within the rail cam by the second portions 410.

With reference to FIGS. 3 and 16 the rail cam 60 is oriented within the cutout such that the cam rotates between a closed/lock position and a open/receive/release position. In FIG. 3, the rail cam is shown in its closed/lock position. When in this position, the lock surface 410 (FIG. 18d) of each arm 62 is substantially flush with the top and bottom surfaces 306, 312 of the first recess, respectively and the second portion 410 of each arm extends into the space between the top and bottom surfaces. When the rail cam is in its open/receive/release position, the release surface 412 of each arm is substantially flush with the top and bottom surfaces 306, 312 of the first recess, respectively and the second portion 410 of each arm 62 is positioned within the top and bottom arcuate region 310, 316, respectively and thus is outside the space between top and bottom surfaces. In a preferred embodiment, the rail cam 60 is formed of plastic and is capable of supporting between 20 to 30 pounds (9 to 13.5 kilograms). To support heavier weights the rail cam may be made of metal.

As shown in FIGS. 16 and 17, the MDI 48 further includes a lever assembly 326 coupled to the rail cam 60. The lever assembly 326 includes an external release lever 66 positioned on the exterior side of the MDI. The external release lever 66 is coupled to an internal release lever 328 positioned beneath the external release lever on the interior side of the MDI. The lever assembly 326 further includes a rail cam lever 330 coupled to the rail cam 60 and positioned on the interior side of the MDI. The rail cam lever 330 is biased in the closed/lock position by a spring 334. The rail cam lever 330 and internal release lever 328 are coupled together by a release linkage 332. Rotation of the external release lever 66 induces rotation of the internal release lever 332 which in turn displaces the release linkage 332. Displacement of the release linkage 332 causes the rail cam lever 330 to rotate against the force of the spring 334 which in turn rotates the rail cam 60. Movement of the lever 66 rotates the rail cam 60 from its closed/lock position to its open/receive/release position.

With reference to FIGS. 3, 16 and 17, the mounting case 50 has a second portion 54 protruding rearward from the case. The second portion 54 includes a second recess 58 defined by a substantially planar top surface 336 and a substantially planar bottom surface 338. The second recess 58 has a height defined by the distance between the top and bottom planar surfaces 336, 338. As with the first recess 56, the height of the second recess 58 is slightly greater than the height of a mounting rail 26. The second recess 58 is aligned with the first recess such that a mounting rail 26 may be positioned within both recesses simultaneously. The first portions 52 and second portion 54 are spaced apart to allow for placement of a portion of the pole clamp assembly 72 there between. Positioned between the first portion 52 and the second portion 54 is a pole clamp recess 340. The pole clamp recess 340 has a generally arcuate surface and is dimensioned and orientated to receive a portion of the pole clamp assembly.

With reference to FIGS. 19a–19d, the pole clamp assembly 72 includes a bracket 500, a pivot member 502 and threaded post 504. The post 504 includes a threaded stud 506 and a handle 508. The bracket 500 is typically mounted to the back panel 72 (FIG. 3) of the MDI 48 near the first and second portions 52, 54. The pivot member 502 is formed in a general L-shape to include a first leg 510 and a second leg 512. The first leg 510 is pivotally mounted to the bracket 500 such that the pivot member 502 is moveable between an open position (FIGS. 19a and 19c) and a closed position (FIGS. 19b and 19d). The second leg 512 carries a threaded hole for receiving the thread stud 506 and allowing for axial movement of the stud.

As shown in FIG. 19c, the bracket 500 has a generally V-shaped cross section. At the point of the V is a stud recess 514 having a semicircular cross section and an axis 516 associated therewith. The second leg 512 of the pivot member is positioned relative the first leg 510 to extend over the bracket 500 such that when the pole clamp assembly 72 is in the closed position, the axis of the stud is substantially parallel with the axis 516 of the stud recess. When the pole clamp assembly is in the closed position, the axis of the post is substantially perpendicular to the axis 516 of the stud recess.

The handle 508 is positioned at one end of the stud 506 and is formed to include opposing curved sides 518 shaped to substantially match the curved shape of the arcuate surface of the pole clamp 340 (FIG. 3). The handle 508 is further formed to include opposing round ends 520. When the pivot member 502 is in a closed position, a portion of the handle 508 and stud 506 lie within the pole clamp recess 340 a portion of the stud resting within the stud recess 514. The pole clamp assembly components are made of metal and may be made by extrusion or casting.

As previously mention and shown in FIG. 4, a medical device 12 is secured to a mounting rail 26 by visually aligning the first recess 56 and the second recess 58 with the mounting rail. Once aligned, the rail cam 60 is pushed against the mounting rail 26. The force of the mounting rail 26 against the sloped guiding portions 64 of the rail cam 60 induces rotation of the rail cam to its open/receive position. In this position the mounting rail is able to slide into the space between the arm bases 404 comes to rest between the lock surfaces 406 the top and bottom surfaces of the first and second recesses 56, 58.

Once the mounting rail 26 is positioned within the rail cam 60, the cam returns to its closed/lock position and the second portions 410 the arms retain the device 12 to the rail. To remove the device 12 from the rail cam, the external release lever 66 is activated to cause the rail cam 60 rotate to its open/release position during which the second portions 410 the arms 62 move into the top and bottom arcuate regions 310, 316, thereby allowing for removal of the device from the mounting rail 26.

During installation of a medical device 12 to a mounting rail 26 the handle 508 may be orientated such one of the rounded end 520 is facing the mounting rail. Orientated as such, the handle 508 may initially interfere with the mounting process by contacting the mounting rail 26 as it is entering the recessed portions 56, 58. However, because of the rounded configuration of the handle end 520, it easily translates the force resulting from the contact between the rounded end 520 and the mounting rail 26 into rotational motion of the handle. The rounded end slides along the surface of the mounting rail while rotating the handle 508 thereby orientating the handle such that one of the curved sides 518 of the handle generally aligns with the arcuate surface defining the pole clamp recess 340 (FIG. 3).

As previously mentioned and shown in FIG. 5, the medical device 12 may be mounted to a pole 74 using the pole clamp assembly 72. In order to do so, the arm 82 of the pole clamp assembly 72 is pivoted to its open position. The medical device 12 is placed on the pole 74 such that the pole lies within the pole clamp assembly recess 340 (FIG. 16) and the bracket 500 (FIG. 19a). The threaded post 84 is then rotated until the tip of the post contacts the pole, thereby clamping the instrument 12 to the pole 74.

It will be apparent from the foregoing that while particular forms of the invention have been illustrated and described, various modifications can be made without department from the spirit and scope of the invention. Accordingly, it is not intended that the invention be limited, except as by the appended claims.

What is claimed is:

1. A docking station for accepting at least one instrument having a housing having a rail cam and a recess and at least one signal port, said docking station comprising:

a casing having a plurality of fastening bars recessed a distance from a front of the casing;

a docking tile secured to the fastening bars;

a mounting rail mounted on the docking tile and spaced a distance therefrom, the mounting rail dimensioned to fit within the housing recess and the rail cam; and at least one tile signal port secured to the tile, a portion of the at least one tile signal port aligned to couple with the at least one housing signal port when the mounting rail is within the housing recess and rail cam, the at least one tile signal port further having a portion for interfacing with a signal source.

2. The docking station of claim 1 wherein the fastening bars comprise channels running a length of the casing and the docking tile may be adjustably positioned along a length of the channels.

3. The docking station of claim 1 further comprising a circuit mounted to a rear of the docking tile, the circuit providing communication between the at least one tile signal port and the signal source.

4. The docking station of claim 3 wherein the at least one tile signal port comprises a power outlet.

5. The docking station of claim 4 wherein the circuit comprises a magnetic relay for feeding power to the power outlet when activated.

6. The docking station of claim 3 wherein the at least one tile signal port comprises a data communications port.

7. The docking station of claim 6 wherein the data communications port comprises an infrared (IR) port.

8. The docking station of claim 1 wherein a plurality of docking tiles are positioned adjacent each ether along a length of the casing, the docking tiles spaced apart to allow for the mounting of a plurality of instruments having a standard height.

9. The docking station of claim 8 further comprising spacing plates positioned between adjacent docking tiles to thereby provide a docking station capable of accepting instruments of non-standard height.

10. The docking station of claim 8 further comprising a base tile for providing signals to each of the plurality of docking tiles.

11. The docking station of claim 10 wherein the base tile comprises a power inlet for receiving external power to be provided to each of the plurality of docking tiles.

12. The docking station of claim 10 wherein the base tile comprises a data communication port for interfacing each of the plurality of docking tiles with an external computer system.

13. The docking station of claim 10 wherein the base tile includes a connection port through which an earth connection is made with the casing.

14. The docking station of claim 1 further comprising means for mounting the casing to a wall.

15. The docking station of claim 1 further comprising a stand having wheels mounted thereon.

16. The docking station of claim 1 further comprising means for hanging bags of infusion fluid.

17. A docking tile for accepting an instrument having a housing having a rail cam and a recess and at least one signal port, said docking tile comprising:

a plate;

a rail mounted on the plate and spaced a distance therefrom, the rail dimensioned to fit within the housing recess and the rail cam; and at least one tile signal port secured to the plate, a portion of the at least one tile signal port aligned to couple with the at least one housing signal port when the rail is within the housing recess and the rail cam, the at least one tile signal port further having a portion for interfacing with a signal source.

18. The docking tile of claim 17 further comprising a circuit for providing communication between the at least one tile signal port and the signal source.

19. The docking tile of claim 18 wherein the at least one tile signal port comprises a power outlet.

20. The docking tile of claim 19 wherein the circuit comprises a magnetic relay for feeding power to the power outlet when activated.

21. The docking tile of claim 18 wherein the at least one tile signal port comprises a data communications port.

22. The docking tile of claim 21 wherein the data communications port comprises an infrared (IR) port.

* * * * *